(12) United States Patent
Mutharasan et al.

(10) Patent No.: US 7,942,056 B2
(45) Date of Patent: May 17, 2011

(54) SELF-EXCITING, SELF-SENSING PIEZOELECTRIC CANTILEVER SENSOR

(75) Inventors: Rajakkannu Mutharasan, West Chester, PA (US); David Maraldo, Gilbertsville, PA (US); Gossett Augustus Campbell, Conshohocken, PA (US); Kishan Rijal, Harleysville, PA (US)

(73) Assignee: Drexel University, Philadelphia, PA (US)

( * ) Notice: Subject to any disclaimer, the term of this patent is extended or adjusted under 35 U.S.C. 154(b) by 1016 days.

(21) Appl. No.: 11/625,919

(22) Filed: Jan. 23, 2007

(65) Prior Publication Data

US 2007/0169553 A1  Jul. 26, 2007

Related U.S. Application Data

(60) Provisional application No. 60/761,172, filed on Jan. 23, 2006, provisional application No. 60/807,020, filed on Jul. 11, 2006.

(51) Int. Cl.
*G01H 1/00* (2006.01)
(52) U.S. Cl. .......................... 73/579; 73/61.75
(58) Field of Classification Search .............. 73/579, 73/617, 622, 642, 644
See application file for complete search history.

(56) References Cited

U.S. PATENT DOCUMENTS

| | | | | |
|---|---|---|---|---|
| 5,079,199 A | * | 1/1992 | Ochi et al. | 501/135 |
| 5,162,691 A | * | 11/1992 | Mariani et al. | 310/321 |
| 5,283,037 A | * | 2/1994 | Baer et al. | 422/82.01 |
| 5,631,514 A | * | 5/1997 | Garcia et al. | 310/309 |
| 5,719,324 A | * | 2/1998 | Thundat et al. | 73/24.01 |
| 5,742,377 A | * | 4/1998 | Minne et al. | 355/71 |
| 5,825,275 A | * | 10/1998 | Wuttig et al. | 337/139 |
| 5,883,705 A | * | 3/1999 | Minne et al. | 355/71 |
| 6,252,335 B1 | * | 6/2001 | Nilsson et al. | 310/328 |
| 6,289,717 B1 | * | 9/2001 | Thundat et al. | 73/23.2 |
| 6,336,366 B1 | * | 1/2002 | Thundat et al. | 73/514.34 |
| 6,545,273 B1 | * | 4/2003 | Singh et al. | 850/55 |
| 6,589,727 B1 | | 7/2003 | Klenerman et al. | 435/4 |

(Continued)

FOREIGN PATENT DOCUMENTS

EP  0 631 319 A1  12/1994

(Continued)

OTHER PUBLICATIONS

Zhou J. et al., "Zeolite-modified microcantilever gas sensor for indoor air quality control," Sensors and Actuators B, Oct. 1, 2003, 94(3), 337-342.

(Continued)

*Primary Examiner* — Hezron Williams
*Assistant Examiner* — Samir M Shah
(74) *Attorney, Agent, or Firm* — Woodcock Washburn, LLP

(57) ABSTRACT

A piezoelectric cantilever sensor includes a piezoelectric layer and a non-piezoelectric layer, a portion of which is attached to the piezoelectric layer. In one embodiment, one end of the non-piezoelectric layer extends beyond the end of piezoelectric layer to provide an overhang. The overhang piezoelectric cantilever sensor enables increased sensitivity allowing application of the device in more viscous environments, such as liquid media, as well as application in liquid media at higher flow rates than conventional piezoelectric cantilevers. In another embodiment, the sensor includes first and second bases and at least one of the piezoelectric layer and the non-piezoelectric layer is affixed to each of the first and second bases to form the piezoelectric cantilever sensor. In this embodiment, the sensor is robust and exhibits excellent sensing characteristics in both gaseous and liquid media, even when subjected to relatively high flow rates.

15 Claims, 18 Drawing Sheets

U.S. PATENT DOCUMENTS

| | | | |
|---|---|---|---|
| 6,813,815 B2* | 11/2004 | Namerikawa et al. | 29/25.35 |
| 7,061,166 B2* | 6/2006 | Kuniyasu | 310/365 |
| 7,066,004 B1* | 6/2006 | Kohler et al. | 73/1.38 |
| 7,089,813 B2* | 8/2006 | Takeuchi et al. | 73/865 |
| 7,195,909 B2 | 3/2007 | Klenerman et al. | 435/287.2 |
| 7,262,546 B2* | 8/2007 | Namerikawa et al. | 310/366 |
| 7,263,874 B2 | 9/2007 | Fitch et al. | 73/54.25 |
| 7,329,536 B2* | 2/2008 | Zeng et al. | 435/287.2 |
| 7,458,265 B2* | 12/2008 | Shih et al. | 73/579 |
| 7,522,029 B1* | 4/2009 | Lantz | 337/139 |
| 7,779,707 B2* | 8/2010 | Shih et al. | 73/862.639 |
| 2002/0170290 A1* | 11/2002 | Bright et al. | 60/527 |
| 2003/0194697 A1 | 10/2003 | Klenerman et al. | 435/5 |
| 2003/0224551 A1 | 12/2003 | Kim et al. | 438/49 |
| 2004/0112723 A1* | 6/2004 | Jung et al. | 200/61.02 |
| 2005/0248235 A1* | 11/2005 | Namerikawa et al. | 310/328 |
| 2005/0277852 A1 | 12/2005 | Shih et al. | 600/587 |
| 2006/0053870 A1 | 3/2006 | Berndt | 73/61.75 |
| 2006/0123910 A1* | 6/2006 | Cunningham et al. | 73/580 |
| 2006/0228657 A1 | 10/2006 | Masters et al. | 430/954 |
| 2007/0089515 A1* | 4/2007 | Shih et al. | 73/579 |
| 2007/0089519 A1* | 4/2007 | Hao et al. | 73/649 |
| 2007/0169553 A1* | 7/2007 | Mutharasan et al. | 73/579 |
| 2007/0218534 A1 | 9/2007 | Klenerman et al. | 435/173.7 |
| 2008/0035180 A1* | 2/2008 | Mutharasan et al. | 134/32 |
| 2008/0144364 A1* | 6/2008 | Lee et al. | 365/164 |

FOREIGN PATENT DOCUMENTS

| | | |
|---|---|---|
| EP | 1 536 227 A2 | 6/2005 |
| WO | WO 98/50773 A2 | 11/1998 |
| WO | WO2005/043126 A2 | 5/2005 |
| WO | WO 2005/043126 A3 | 5/2005 |

OTHER PUBLICATIONS

Yi Jeong W. et al., "In situ cell detection using piezoelectric lead zirconate titanate-stainless steel cantilevers," J Applied Physics, Jan. 1, 2003, 93(1), 619-625.

Campbell et al., "Detection of pathogen *Escherichia coli* O157:H7 using self-excited PZT-glass microcantilevers," Biosensors & Bioelectronics, Sep. 15, 2005, 21(3), 462-473.

Seung S. Lee, et al., "Self-excited piezoelectric cantilever oscillators," Transducers, 1995, 417-420.

U.S. Appl. No. 11/659,919, filed Jan. 23, 2007, Mutharasan, et al.
U.S. Appl. No. 11/747,183, filed May 10, 2007, Mutharasan, et al.
U.S. Appl. No. 60/746,951, filed May 10, 2006, Mutharasan, et al.
U.S. Appl. No. 60/761,172, filed Jan. 23, 2006, Mutharasan, et al.
U.S. Appl. No. 60/807,020, filed Jul. 11, 2006, Mutharasan, et al.

Campbell, G.A., et al., "Piezoelectric excited millimeter-sized cantilever (PEMC) sensor detects *Escherichia coli* O157:H7 in two-hour incubated samples at 4 CFU per gram of beef," J. of Rapid Methods and Automation in Mirobiology, 1-39, 2005.

Campbell, G.A., et al., "Detection and quantification of proteins using self-excited PZT-glass millimeter-sized cantilever," Biosensors and Bioelectronics, 26-36, 2004.

Campbell, G.A., "Piezoelectric-excited millimeter-sized cantilever (PEMC) sensors detect *Bacillus anthracis* at 300 spores/mL," Biosensors and Bioelectronics, 37-45, 2005.

Campbell, G.A., et al., "Kinetics of *Bacillus anthracis* spore binding to antibody functionalized PEMC sensors in presence of *Bacillus thuringiensis* and *Bacillus cereus*," J. Publications, Am. Chem. Soc., 25 pages, 2006.

Campbell, G.A., et al., "*Escherichia coli* O157:H7 detection limit of millimeter-sized PZT cantilever sensors in 700 cells/mL," Analytical Sci., 11-13, 2005.

Campbell, G.A., et al., "Detection of pathogen *Escherichia coli* O157:H7 using self-excited PZT-glass microcantilevers," Biosensors and Bioelectronics, 14-25, 2004.

Campbell, G.A., "Detection of *Staphylococcus* enterotoxin B at pictogram levels using piezoelectric-excited millimeter-sized cantilever sensors," Submitted on-line to J. of Analytical Chem, 1-24, 2006.

Campbell, G.A., et al., "Detect *Escherichia coli* O157:H7 in ground beef samples using piezoelectric excited millimeter-sized cantilever (PEMC) sencors," Submitted on-line to Biosensors and Bioelectronics, 2-34, 2006.

Campbell, G.A., et al.,"A method for measuring *Escherichia coli* O157:H7 at 1 cell/mL in 1 liter sample using antibody functional piezoelectric-excited millimeter-sized cantilever sensor," Paper submitted on-line to J. of Analytical Chemistry, 1-23, 2006.

Carr, D.W., et al., "Fabrication of nanoelectromechanical systems in single crystal silicon using silicon on insulator substrates and electron beam lithography," J. Vac. Sci. Technology, B, 5(6), 2760-2763, 1997.

Maraldo,D., et al., "Resonant-mode millimeter-sized cantilever biosensor for continuous detection of proteins and pathogens in flowing liquids," Dept. of Chem. And Biological Eng., 1-21, 2006.

Wilson, L., et al., "Piezoelectric-excited millimeter-sized cantilever (PEMC) sensor provides viscosity and density measurements," Submitted to Review of Scientific Instruments, 1-26, 2005.

\* cited by examiner

SELF-EXCITING, SELF-SENSING PIEZOELECTRIC CANTILEVER SENSOR

CROSS REFERENCE TO RELATED APPLICATIONS

The present application claims priority to U.S. Provisional Patent application No. 60/761,172, entitled "PIEZOELECTRIC CANTILEVER SENSORS," filed Jan. 23, 2006, and U.S. Provisional Patent Application No. 60/807,020, entitled "PIEZOELECTRIC CANTILEVER SENSORS," filed Jul. 11, 2006, both of which are hereby incorporated by reference in their entirety.

TECHNICAL FIELD

The technical field generally relates to sensors, and more specifically relates to piezoelectric cantilever sensors and to detecting and measuring analytes utilizing a piezoelectric cantilever sensor.

BACKGROUND

Cantilever sensors can be broadly divided into two categories, depending upon dimensions of the sensor: micro-cantilevers and macro-cantilevers. Micro-cantilever sensors can be utilized in both static (bending) mode and dynamic (resonance) mode. In static mode, the deformation of the cantilever arm is measured to determine if an analyte (substance under analysis) is present. In dynamic mode, a resonance frequency is measured to determine if an analyte is present. Macro-cantilever sensors typically are not utilized in the static mode because bending of the cantilever arm is often limited. Macro-cantilever sensors can be utilized under liquid immersion conditions or in a gas or vacuum. Typically, greater sensitivity is achievable when a cantilever sensor is utilized in a gas/vacuum than in a liquid. Liquid dampening tends to adversely affect sensitivity. However, measuring analytes in liquid medium has many practical applications.

One type of known micro-cantilever sensor is a silicon-based micro-cantilever sensor. A typical silicon-based micro-cantilever sensor comprises a micro-cantilever that acts as a resonator. The micro-cantilever is driven by an external actuator at the base of the micro-cantilever to generate vibrations in the resonator. Typically, the vibrations are detected by an external optical detector. One disadvantage of typical silicon-based micro-cantilevers is the complex external optical components required for detection. Further, optical detection means disadvantageously limit application of the micro-cantilever sensor to optically clear samples. Another disadvantage is the weight and complexity added to the sensor due to the external actuator. Yet another disadvantage is that the external actuator can be located only at the base of the micro-cantilever, which limits its effectiveness in driving the cantilever's vibration. A further disadvantage of silicon-based micro-cantilever sensors is that they are mechanically fragile. Thus, silicon-based micro-cantilever sensors can not be used in high liquid flow rate environments. Further, typical silicon-based micro-cantilever sensors lose detection sensitivity in liquid media due to viscous damping.

Another type of known cantilever sensor is a quartz-based piezoelectric cantilever sensor. Quartz is a weak piezoelectric, and thus, much like silicon-based cantilever sensors, quartz-based piezoelectric cantilever sensors lose detection sensitivity in liquid media due to viscous damping. Further, the detection sensitivity of quartz-based sensors is limited by the planar geometry of the sensor.

Conventional piezoelectric cantilevers are known to be fabricated with a piezoelectric layer attached to a non-piezoelectric layer over part or the entire surface of the piezoelectric layer. In some conventional piezoelectric cantilevers, the piezoelectric layer is fixed at one end so that when the piezoelectric material is excited, the non-piezoelectric layer flexes to accommodate the strain caused in the piezoelectric material. When the frequency of excitation is the same as the natural frequency of the underlying mechanical structure, resonance occurs. This type of piezoelectric cantilever sensor is known to operate at frequencies lower than about 100 kHz at millimeter size. Currently, higher frequencies are obtainable only by making the cantilever sensor very short (less than 1.0 mm in length), very narrow (less than 0.1 mm in width), and very thin (less than 100 microns in thickness). However, reducing the dimensions of the cantilever sensor, particularly the width, thusly, makes the cantilever sensor less usable in a liquid medium due to viscous damping. Damping increases inversely with square of cantilever width.

SUMMARY

A self-exciting and self-sensing piezoelectric cantilever sensing apparatus includes a piezoelectric layer and a non-piezoelectric layer attached to the piezoelectric layer such that a distal end of the non-piezoelectric layer extends beyond a distal end of the piezoelectric layer or a distal end of the piezoelectric layer extends beyond a distal end of the non-piezoelectric layer. That is, the piezoelectric layer is coupled to the non-piezoelectric layer such that the piezoelectric layer and the non-piezoelectric layer are not coextensive In various configurations of the piezoelectric cantilever sensing apparatus, the piezoelectric layer, the non-piezoelectric layer, or both are anchored to at least one base. Electrodes are operatively associated with the piezoelectric layer. The self-exciting, self-sensing piezoelectric cantilever sensor is utilized to sense mass change. To determine the mass of an analyte on the sensing apparatus, the resonance frequency of the mechanical member of the cantilever sensor is measured. The measured resonance frequency is compared with a baseline resonance frequency to determine a difference in frequency. The difference in frequency is indicative of a mass of an analyte on the sensing apparatus.

BRIEF DESCRIPTION OF THE DRAWINGS

The foregoing summary, as well as the following detailed description, is better understood when read in conjunction with the appended drawings. For the purpose of illustrating a self-exciting, self-sensing piezoelectric cantilever sensor, there is shown in the drawings exemplary constructions thereof, however, a self-exciting, self-sensing piezoelectric cantilever sensor is not limited to the specific methods and instrumentalities disclosed.

DETAILED DESCRIPTION OF ILLUSTRATIVE EMBODIMENTS

Figure 1:
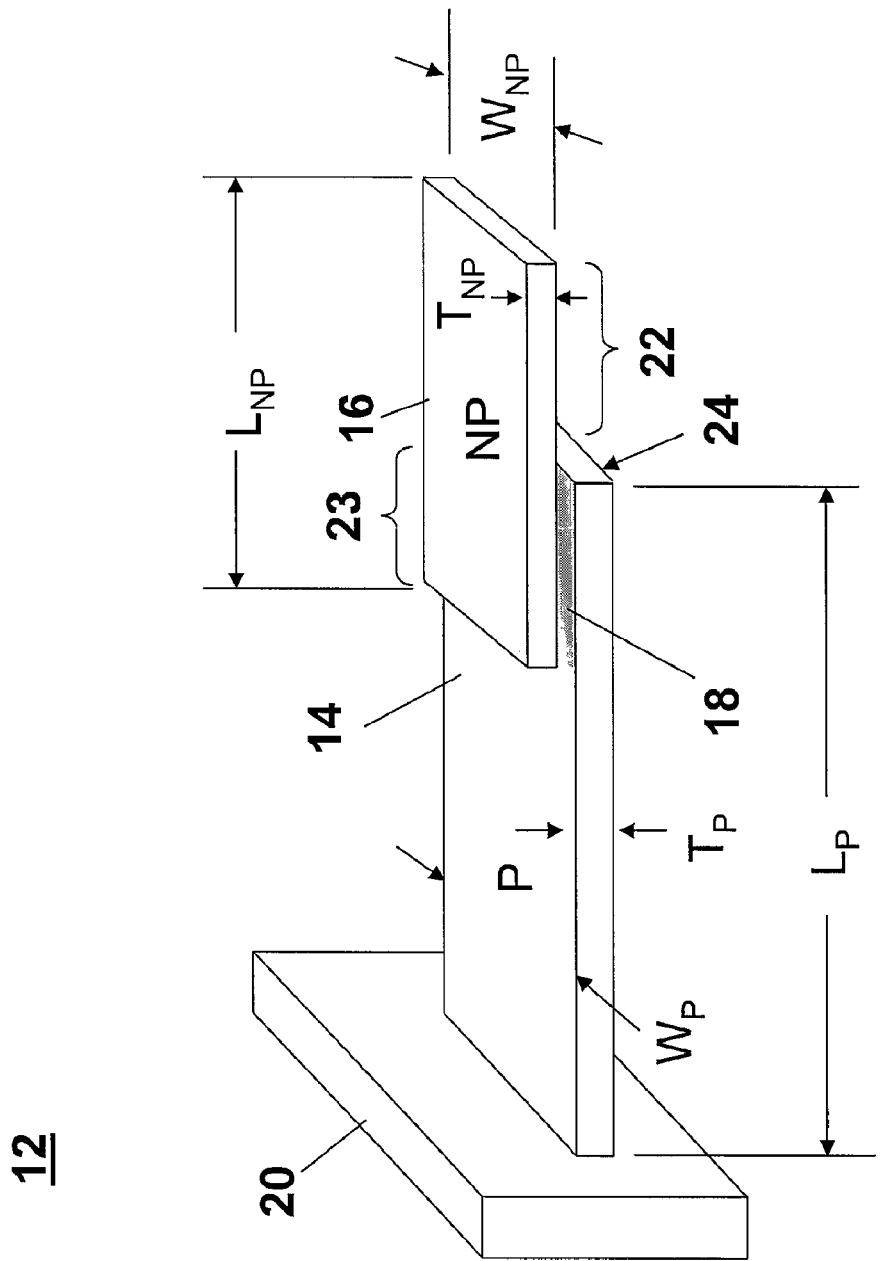
FIG. 1 is an illustration of an example configuration of a self-exciting, self-sensing piezoelectric cantilever sensor.

A self-exciting, self-sensing piezoelectric cantilever sensor as described herein provides the ability to detect and measure extremely small amounts of an analyte. The self-exciting, self-sensing piezoelectric cantilever sensor can be utilized to detect and measure an analyte immersed in a liquid and an analyte contained in a gas or vacuum. In various example configurations, the self-exciting, self-sensing piezoelectric cantilever sensor comprises at least one piezoelectric layer and at least one non-piezoelectric layer, wherein the piezoelectric layer is coupled to the non-piezoelectric layer such that the piezoelectric layer and the non-piezoelectric layer are not coextensive. The piezoelectric layer, the non-piezoelectric layer, or both can be coupled to at least one base. The piezoelectric layer and the non-piezoelectric layer can be of varying widths, lengths, and thicknesses.

The self-exciting, self-sensing piezoelectric cantilever sensor is utilizable to determine the mass of an analyte accumulated thereon. In an example embodiment, a portion of the self-exciting, self-sensing piezoelectric cantilever sensor is placed in a medium (e.g., liquid, gas, vacuum). While in the medium, a resonance frequency of the self-exciting, self-sensing piezoelectric cantilever sensor is measured and compared to a baseline resonance frequency. The difference in the measured resonance frequency and the baseline resonance frequency is indicative of an amount of mass of analyte accumulated (e.g., bound, adsorbed, absorbed) on the self-exciting, self-sensing piezoelectric cantilever sensor.

Analytes can be directly or indirectly bound to the surface of the non-piezoelectric portion of the self-exciting, self-sensing piezoelectric cantilever sensor. Binding of an analyte to the non-piezoelectric portion of the self-exciting, self-sensing piezoelectric cantilever sensor results in a change in mass of the self-exciting, self-sensing piezoelectric cantilever sensor, a change in stiffness of the self-exciting, self-sensing piezoelectric cantilever sensor, or a combination thereof. The changes in mass and/or stiffness are measurable as changes in resonance frequency, and can be monitored and measured by an appropriate analysis device, such as an operational amplifier, an impedance analyzer, a network analyzer, an oscillator circuit, or the like, for example. Resonance frequency changes, wherein at least a portion of the self-exciting, self-sensing piezoelectric cantilever sensor is immersed in a liquid, are detectable and measurable. Resonance frequency changes, wherein at least a portion of the self-exciting, self-sensing piezoelectric cantilever sensor is immersed in a gas or a vacuum, also are detectable and measurable.

The self-exciting, self-sensing piezoelectric cantilever sensor is operateable at high frequencies, such as, on the order of 0.1 MHz. to 6 MHz, for example. At these high frequencies, a Q factor (the ratio of the resonance peak frequency relative to the resonance peak width at half peak height), on the order of 10 to 100, under liquid immersion is obtainable. The self-exciting, self-sensing piezoelectric cantilever sensor is operateable at relative high frequencies in liquid media, gas media, and a vacuum. The self-exciting, self-sensing piezoelectric cantilever sensor thus provides extreme sensitivity to mass changes. The self-exciting, self-sensing piezoelectric cantilever sensor is especially suitable for analytes that are present at very low concentrations in media such as in body fluids, water, and food materials, for example.

The self-exciting, self-sensing piezoelectric cantilever sensor described herein provides the ability to detect changes in mass accumulated thereon as small as 100 attogram/Hz (100× $10^{-18}$ grams/Hertz) or less when immersed in a liquid media. Thus, with respect to detecting changes in mass, the self-exciting, self-sensing piezoelectric cantilever sensor is approximately 1 million times more sensitive than a quartz crystal micro-cantilever sensor, approximate 100,000 times more sensitive than standard analytical instruments, and about 10,000 times more sensitive than conventional, three-layer piezoelectric cantilever designs.

The self-exciting, self-sensing piezoelectric cantilever sensor permits detection of extremely small concentrations of analyte that bind to the non-piezoelectric portion thereof. Utilizing the self-exciting, self-sensing piezoelectric cantilever sensor, pathogens and proteins are detectable at concentrations as low as a few pathogens/mL and, for proteins of average size (60 kilo-Daltons, kDa), at less than 1 pathogen/mL. Furthermore, any analyte that binds to an organic or inorganic functional group on the non-piezoelectric portion is detectable. The self-exciting, self-sensing piezoelectric cantilever sensor is operable in media having relatively high flow rates. The piezoelectric cantilevers sensors is operable in media having flow rates of 0.5 to 10.0 mL/minute, which is approximately 1000 times the flow rate used successfully with known bending mode micro-cantilevers.

Various example applications of the piezoelectric cantilever include the detection of bioterrorism agents, such as *Bacillus anthracis*, the detection of food-borne pathogens, such as *E. coli*, the detection of pathogens in food and water, the detection of certain cell types in body fluids (e.g., circulating tumor cells), the detection of biomarkers in body fluids (e.g., proteins that mark specific pathophysiology-alpha-fetoprotein, beta-2-microglobulin, bladder tumor antigen, breast cancer marker CA-15-3, and other CAs (cancer antigens), calcitonin, carcinoembryonic antigen, and others), the detection of markers of explosives such as trinitrotoluene, the presence of dinitrotoluene, and the detection of airborne and waterborne toxins. The self-exciting, self-sensing piezoelectric cantilever sensor also can be used for the detection of biological entities at picogram levels, and for the detection of protein-protein interactions, both steady state and kinetic.

Pathogens, such as *E-coli* for example, are detectable utilizing the self-exciting, self-sensing piezoelectric cantilever sensor. Detection of a model protein, lipoprotein, DNA, and/or RNA at a concentration 1.0 femtogram per mL ($10^{-15}$ grams) and pathogens at 1 pathogen/mL, respectively is achievable by measuring directly in liquid using the self-exciting, self-sensing piezoelectric cantilever sensor immobilized with antibodies specific to the target analyte at a frequency of about 1 to 2 MHz. The self-exciting, self-sensing piezoelectric cantilever sensor is capable of detecting a target analyte without false positives or negatives even when contaminating entities are present. The self-exciting, self-sensing piezoelectric cantilever sensor described herein is particularly advantageous when utilized with a raw sample, and no preparation, concentrating step, and/or enrichment of any type. Detection of an analyte utilizing the self-exciting, self-sensing piezoelectric cantilever sensor can be conducted directly in raw samples under flow conditions, such as 0.5 to 10.0 mL/minute for example. If clean samples are available, such as in a laboratory environment, detection at 1 femtogram/mL is achievable. This sensitivity is approximately 100 times more sensitive than the sensitivity associated with known optical techniques.

As described below, the sensitivity of the self-exciting, self-sensing piezoelectric cantilever sensor is due in part to the geometric design thereof. The relative lengths and widths of the piezoelectric and non-piezoelectric layers of the self-exciting, self-sensing piezoelectric cantilever sensor determine the sensitivity, and also the shape of the peak of the frequency spectrum provided by the self-exciting, self-sensing piezoelectric cantilever sensor. As described in more detail below, the self-exciting, self-sensing piezoelectric cantilever sensor comprises a piezoelectric layer and a non-piezoelectric layer coupled together such that a portion of the piezoelectric layer extends beyond the non-piezoelectric layer, or a portion of the non-piezoelectric layer extends beyond the piezoelectric layer, or a combination thereof. Thus, the piezoelectric layer and the non-piezoelectric layer are not coextensive. That is, the self-exciting, self-sensing piezoelectric cantilever sensor is configured such that an entire surface of the non-piezoelectric layer is not coupled to an entire surface of the piezoelectric layer.

The sensitivity of the self-exciting, self-sensing piezoelectric cantilever sensor is due in part to utilizing the piezoelectric layer of the cantilever sensor for both actuation and sensing and the electromechanical properties of the piezoelectric layer of the self-exciting, self-sensing piezoelectric cantilever sensor. At resonance, the oscillating cantilever concentrates stress in the piezoelectric layer toward a base portion of the self-exciting, self-sensing piezoelectric cantilever. This results in an amplified change in the resistive component of the piezoelectric layer, and a large shift in resonance frequency. Directing this stress to a portion of the piezoelectric layer having a low bending modulus (e.g., more flexible) allows for exploitation of the associated shift in resonance frequency to detect extremely small changes in mass of the self-exciting, self-sensing piezoelectric cantilever sensor. For example, if both the piezoelectric layer and the non-piezoelectric layer of a piezoelectric cantilever sensor are anchored at the same end (e.g., potted in epoxy), the sensor is less sensitive to changes in mass because the bending stress in the sensing piezoelectric layer proximal to the anchored end is lower compared to the case when only the piezoelectric layer is anchored. This is because the bending modulus of the two combined layers is higher than the case of anchoring the piezoelectric layer only. Bending modulus is the product of elastic modulus and moment of inertia about the neutral axis. And, moment of inertia is proportional to the cube power of thickness.

FIG. 1 is an illustration of a self-exciting, self-sensing piezoelectric cantilever sensor 12 comprising a piezoelectric portion 14 and a non-piezoelectric portion 16. Piezoelectric portions are labeled with an uppercase letter p ("P"), and non-piezoelectric portions are labeled with the uppercase letters np ("NP"). The self-exciting, self-sensing piezoelectric cantilever sensor 12 depicts an embodiment of an unanchored, overhang, self-exciting, self-sensing piezoelectric cantilever sensor. The self-exciting, self-sensing piezoelectric cantilever sensor 12 is termed "unanchored" because the non-piezoelectric layer 16 is not attached to the base portion 20. The self-exciting, self-sensing piezoelectric cantilever sensor 12 is termed, "overhang" because the non-piezoelectric layer 16 extends beyond the distal tip 24 of the piezoelectric layer 14 to create an overhanging portion 22 of the non-piezoelectric layer 16. The piezoelectric portion 14 is coupled to the non-piezoelectric portion 16 via adhesive portion 18. The piezoelectric portion 14 and the non-piezoelectric portion overlap at region 23. The adhesive portion 18 is positioned between the overlapping portions of the piezoelectric portion 14 and the non-piezoelectric portion 16. The piezoelectric portion 14 is coupled to a base portion 20.

The piezoelectric portion 14 can comprise any appropriate material such as lead zirconate titanate, lead magnesium niobate-lead titanate solid solutions, strontium lead titanate, quartz silica, piezoelectric ceramic lead zirconate and titanate (PZT), piezoceramic-polymer fiber composites, or the like, for example. The non-piezoelectric portion 16 can comprise any appropriate material such as glass, ceramics, metals, polymers and composites of one or more of ceramics, and polymers, such as silicon dioxide, copper, stainless steel, titanium, or the like, for example.

The self-exciting, self-sensing piezoelectric cantilever sensor can comprise portions having any appropriate combination of dimensions. Further, physical dimensions can be non-uniform. Thus, the piezoelectric layer and/or the non-piezoelectric layer can be tapered. For example, the length (e.g., $L_P$ in FIG. 1) of the piezoelectric portion (e.g., piezoelectric portion 14) can range from about 0.1 to about 10 mm. The length (e.g., $L_{NP}$ in FIG. 1) of the non-piezoelectric portion (e.g., non-piezoelectric portion 16) can range from about 0.1 to about 10 mm. The overlap region (e.g., overlap region 23) can range from about 0.1 to about 10 mm in length. The width (e.g., $W_P$ in FIG. 1) of the piezoelectric portion (e.g., piezoelectric portion 14), and the width (e.g., $W_{NP}$ in FIG. 1) of the non-piezoelectric portion (e.g., non-piezoelectric portion 16), can range from about 0.1 mm to about 4.0 mm. The width (e.g., $W_P$ in FIG. 1) of the piezoelectric portion can differ from the width (e.g., $W_{NP}$ in FIG. 1) of the non-piezoelectric portion as well. The thickness of the (e.g., $T_P$ in FIG. 1) of the piezoelectric portion (e.g., piezoelectric portion 14), and the thickness (e.g., $T_{NP}$ in FIG. 1) of the non-piezoelectric portion (e.g., non-piezoelectric portion 16), can range from about 0.1 mm to about 4.0 mm. The thickness (e.g., $T_P$ in FIG. 1) of the piezoelectric portion also can differ from the thickness (e.g., $T_{NP}$ in FIG. 1) of the non-piezoelectric portion.

Figure 2:
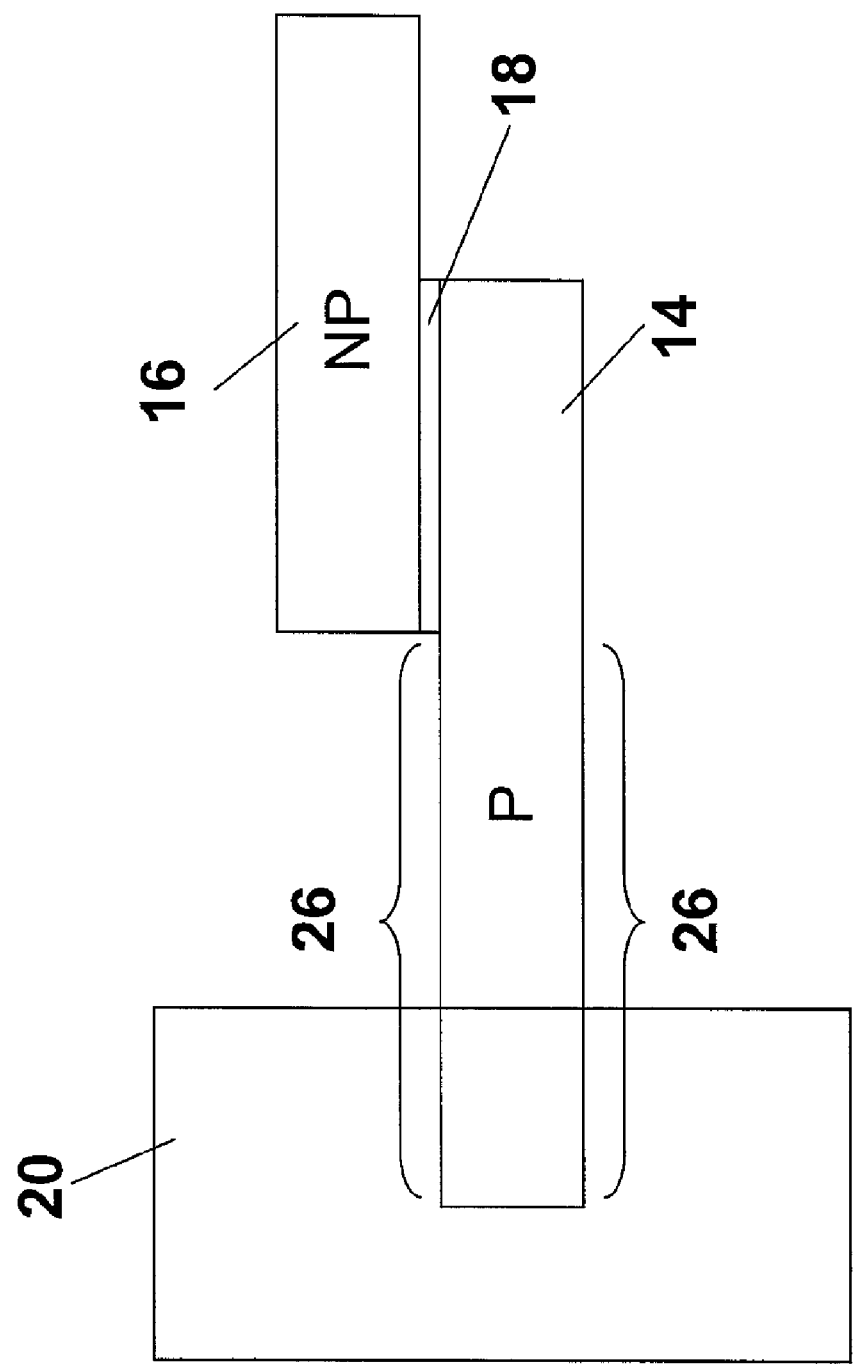
FIG. 2 is a cross-sectional view of an example self-exciting, self-sensing piezoelectric cantilever sensor depicting electrode placement regions for electrodes operationally associated with the piezoelectric layer.
Figure 3:
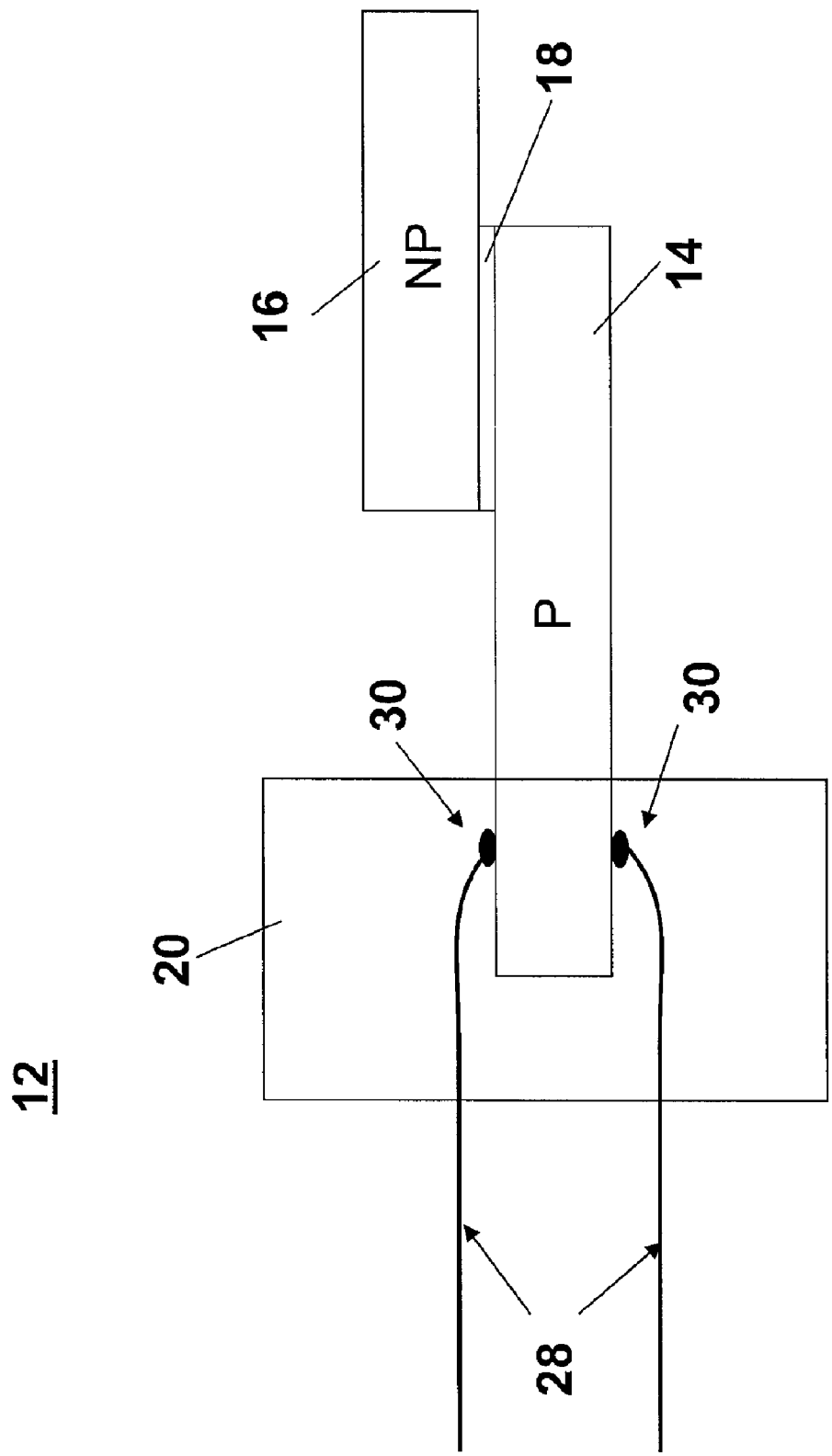
FIG. 3 is a cross-sectional view of an example self-exciting, self-sensing piezoelectric cantilever sensor showing depicting example electrode placement within a base portion of the self-exciting, self-sensing piezoelectric cantilever sensor.
Figure 4:
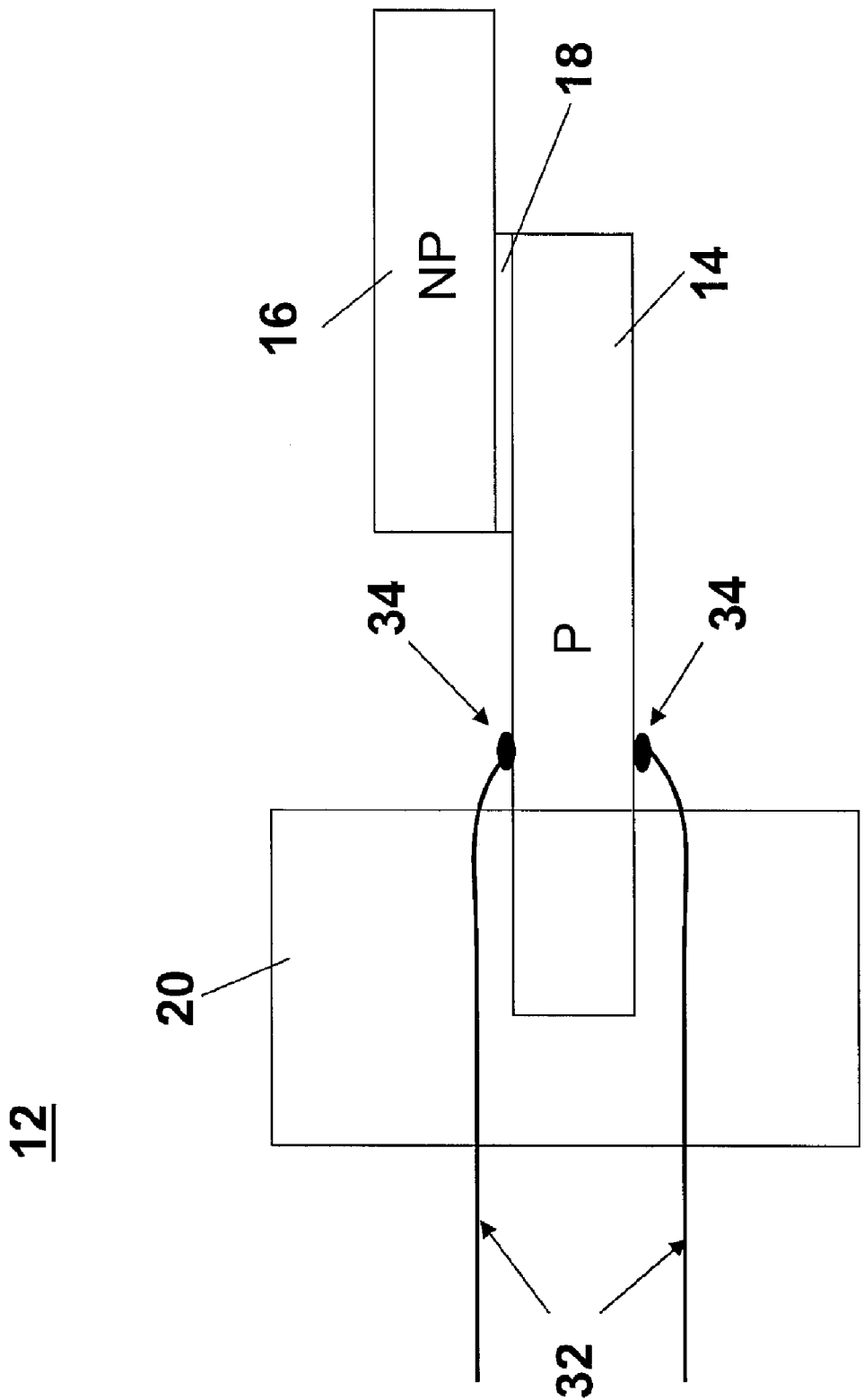
FIG. 4 is a cross-sectional view of an example self-exciting, self-sensing piezoelectric cantilever sensor showing depicting example electrode placement not within a base portion of the self-exciting, self-sensing piezoelectric cantilever sensor.

FIG. 2 is a cross-sectional view of the self-exciting, self-sensing piezoelectric cantilever sensor 12 depicting electrode placement regions 26 for electrodes operationally associated with the piezoelectric portion 14. Electrodes can be placed at any appropriate location on the piezoelectric portion of the self-exciting, self-sensing piezoelectric cantilever sensor as indicated by brackets 26. For example, as shown in FIG. 3, electrodes 28 can be coupled to the piezoelectric portion 14 within the base portion 20. Or, as depicted in FIG. 4, electrodes 32 can be coupled to the piezoelectric portion 14 at any location not within the base portion 20 and not overlapped by the non-piezoelectric portion 16. Electrodes need not be placed symmetrically about the piezoelectric portion 14. In an example embodiment, one electrode can be coupled to the piezoelectric portion 14 within the base portion 20 and the other electrode can be coupled to the piezoelectric portion 14 not within the base portion 20. Electrodes, or any appropriate means (e.g., inductive means, wireless means), can be utilized to provide an electrical signal to and receive an electrical signal from the piezoelectric portion 14. In an example embodiment, electrodes can be coupled to the piezoelectric portion 14 via a bonding pad or the like (depicted as elements 30 in FIG. 3 and elements 34 in FIG. 4). Example bonding pads can comprise any appropriate material (e.g., gold, silicon oxide) capable of immobilization of a receptor material and/or an absorbent material appropriate for use in chemical sensing or for bio-sensing.

Electrodes can be placed at any appropriate location. In an example embodiment, electrodes are operatively located near a location of concentrated stress in the piezoelectric layer 14. As described above, the sensitivity of the self-exciting, self-sensing piezoelectric cantilever sensor is due in part to advantageously directing (concentrating) the stress in the piezoelectric layer 14 and placing electrodes proximate thereto. The configurations of the self-exciting, self-sensing piezoelectric cantilever sensor described herein (and variants thereof) tend to concentrate oscillation associated stress in the piezoelectric layer 14. At resonance, in some of the configurations of the self-exciting, self-sensing piezoelectric cantilever sensor, the oscillating cantilever concentrates stress in the piezoelectric layer 14 toward the base portion 20. This results in an amplified change in the resistive component of the piezoelectric layer 14, and a large shift in resonance frequency at the locations of high stress. Directing this stress to a portion of the piezoelectric layer 14 having a low bending modulus (e.g., more flexible) allows for exploitation of the associated shift in resonance frequency to detect extremely small changes in mass of the self-exciting, self-sensing piezoelectric cantilever sensor. Thus, in example configurations of the self-exciting, self-sensing piezoelectric cantilever sensor, the thickness of the piezoelectric layer 14 located near the base portion 20 is thinner than portions of the piezoelectric layer 14 further away from the base portion 20. This tends to concentrate stress toward the thinner portion of the piezoelectric layer 14. In example configurations, electrodes are located at or near the locations of the oscillation associated concentrated stress near the base portion of the self-exciting, self-sensing piezoelectric cantilever sensor. In other example configurations of the self-exciting, self-sensing piezoelectric cantilever sensor electrodes are positioned proximate the location of concentrated stress in the piezoelectric layer regardless of the proximity of the concentrated stress to a base portion of the self-exciting, self-sensing piezoelectric cantilever sensor.

Figure 5:
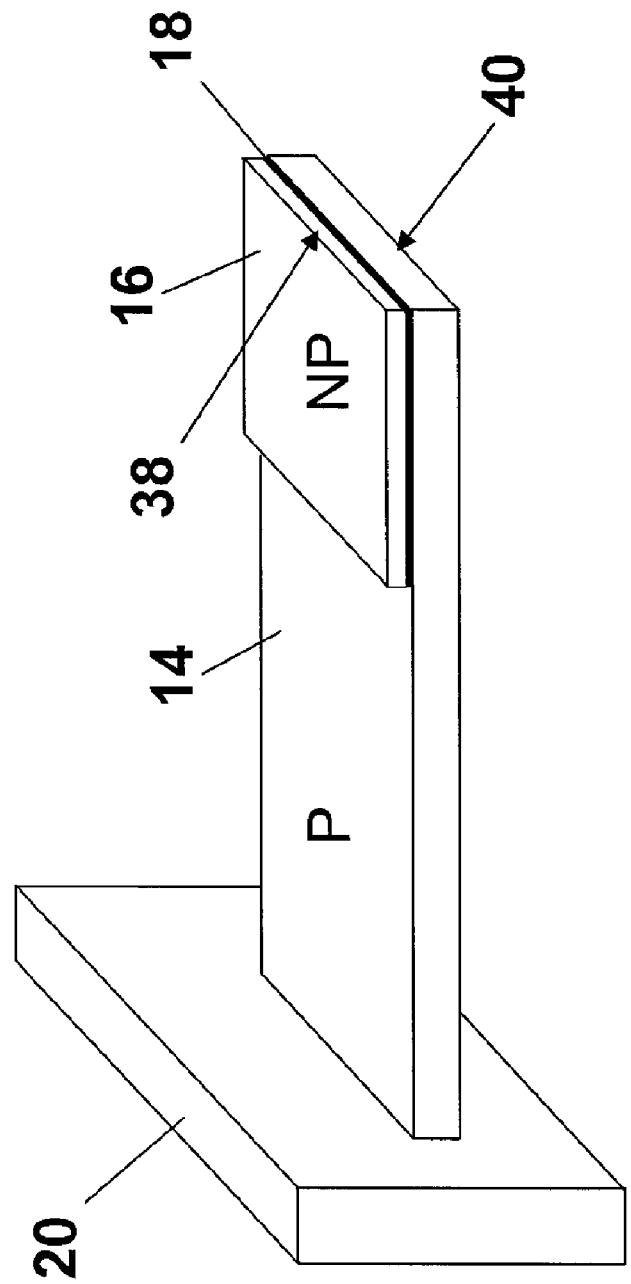
FIG. 5 is an illustration of an example configuration of a self-exciting, self-sensing piezoelectric cantilever sensor wherein the distal end of the piezoelectric layer is flush with the distal end of the non-piezoelectric layer.

The self-exciting, self-sensing piezoelectric cantilever sensor can be configured in accordance with a plurality of configurations, some of which are depicted in FIG. 5 through FIG. 16. It is to be understood however, that the configurations depicted herein do not represent all possible configurations, but rather a representative sample of configurations of the self-exciting, self-sensing piezoelectric cantilever sensor. FIG. 5 is an illustration of an example configuration 36 of an unanchored self-exciting, self-sensing piezoelectric cantilever sensor wherein the distal end 40 of the piezoelectric portion 14 is flush with the distal end 38 of the non-piezoelectric portion 16. The self-exciting, self-sensing piezoelectric cantilever sensor 36 is termed "unanchored" because the non-piezoelectric portion 16 is not attached to the base portion 20. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to a base portion 20.

Figure 6:
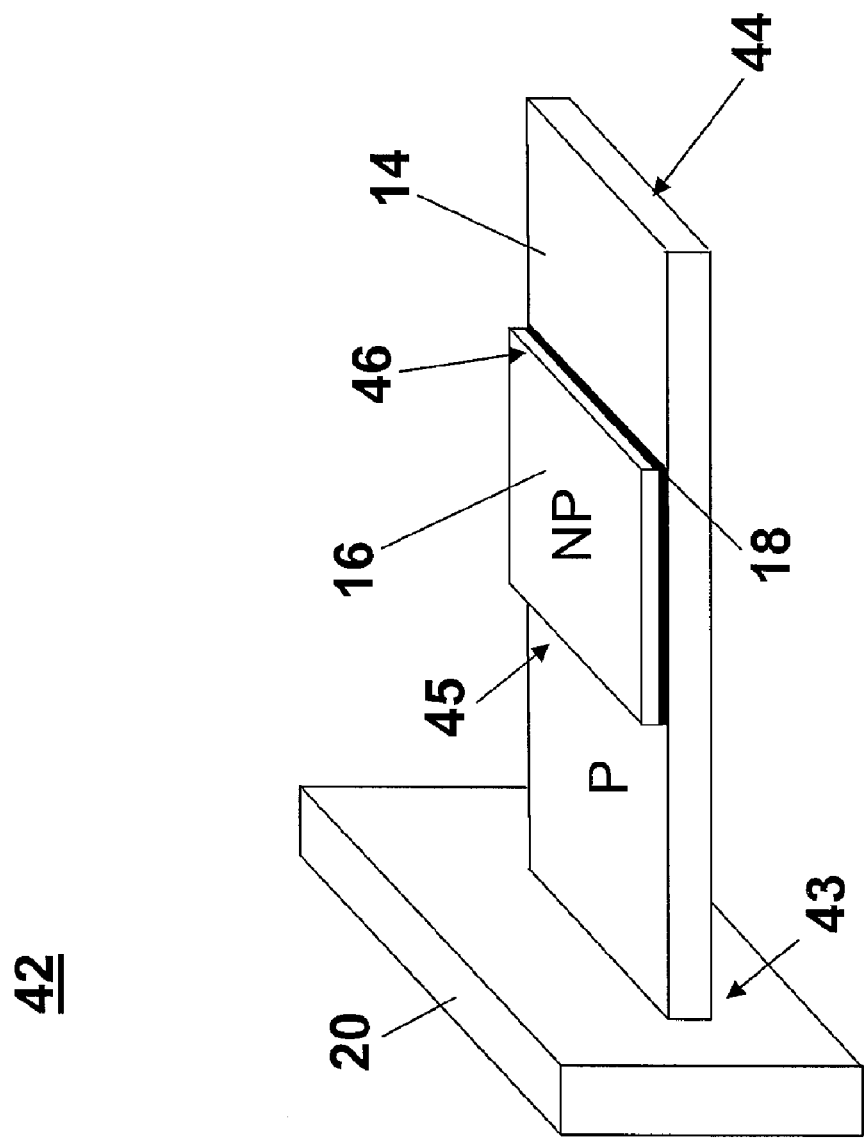
FIG. 6 is an illustration of an example configuration of a self-exciting, self-sensing piezoelectric cantilever sensor wherein the distal end of the piezoelectric layer extends beyond the distal end of the non-piezoelectric layer and the proximate end of the piezoelectric layer extends beyond the proximate end of the non-piezoelectric layer.

FIG. 6 is an illustration of an example configuration 42 of an unanchored self-exciting, self-sensing piezoelectric cantilever sensor wherein the distal end 44 of the piezoelectric portion 14 extends beyond the distal end 46 of the non-piezoelectric portion 16 and the proximate end 43 of the piezoelectric portion 14 extends beyond the proximate end 45 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to the base portion 20.

The self-exciting, self-sensing piezoelectric cantilever sensor also can be configured to comprise multiple base portions. Example configurations of the self-exciting, self-sensing piezoelectric cantilever sensor comprising multiple base portions are depicted in FIG. 7 through FIG. 14. Configuring the self-exciting, self-sensing piezoelectric cantilever sensor to comprise multiple base portions is not intuitive because the expectation of one skilled in the art would be that affixation of both ends of the self-exciting, self-sensing piezoelectric cantilever sensor would provide a poor response as a result of the restrictions of the displacement of the self-exciting, self-sensing piezoelectric cantilever sensor as a result of its affixation to the multiple base portions. For configurations of the self-exciting, self-sensing piezoelectric cantilever sensor comprising two base portions, in an example embodiment, the stress of in the piezoelectric portion is measured, rather than the displacement of the piezoelectric portion. Configuring the self-exciting, self-sensing piezoelectric cantilever sensor to comprise two base portions provides a stable and robust sensor that can perform under relatively high media flow conditions and provide excellent mass change sensitivity. Along with providing a mechanically robust self-exciting, self-sensing piezoelectric cantilever sensor that can withstand a relatively wide range of media flow conditions with minimal determination in performance, configuring the self-exciting, self-sensing piezoelectric cantilever sensor to comprise two base portions provides a fundamental frequency (e.g., greater than 100 kHz) that is three to four times higher than a cantilever sensor having a single base portion and of similar dimensions.

Figure 7:
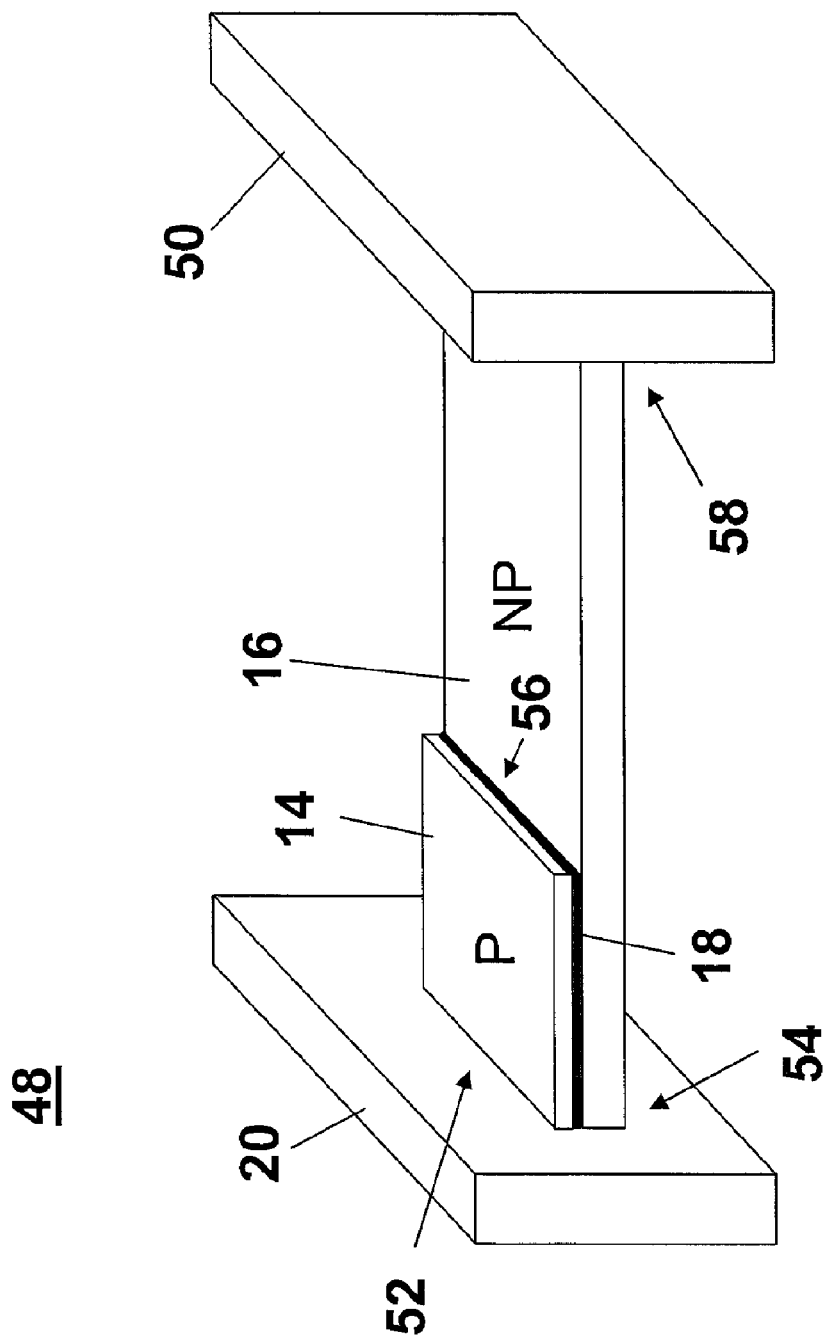
FIG. 7 is an illustration of an example configuration of a self-exciting, self-sensing piezoelectric cantilever sensor having two base portions.

FIG. 7 is an illustration of an example configuration 48 of an anchored self-exciting, self-sensing piezoelectric cantilever sensor comprising two base portions 20, 50. The self-exciting, self-sensing piezoelectric cantilever sensor 48 is termed "anchored" because the non-piezoelectric portion 16 is attached to the base portion 20. In the configuration depicted in the self-exciting, self-sensing piezoelectric cantilever sensor 48, both the proximate end 52 of the piezoelectric portion 14 and the proximate end 54 of the non-piezoelectric portion 16 are attached to the base portion 20. The piezoelectric portion and the non-piezoelectric portion can be attached to the base portion via any appropriate means. The distal end 58 of the non-piezoelectric portion 16 also is attached to the base portion 50. The distal end 58 of the non-piezoelectric portion 16 extends beyond the distal portion 56 of the piezoelectric portion 14. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 8:
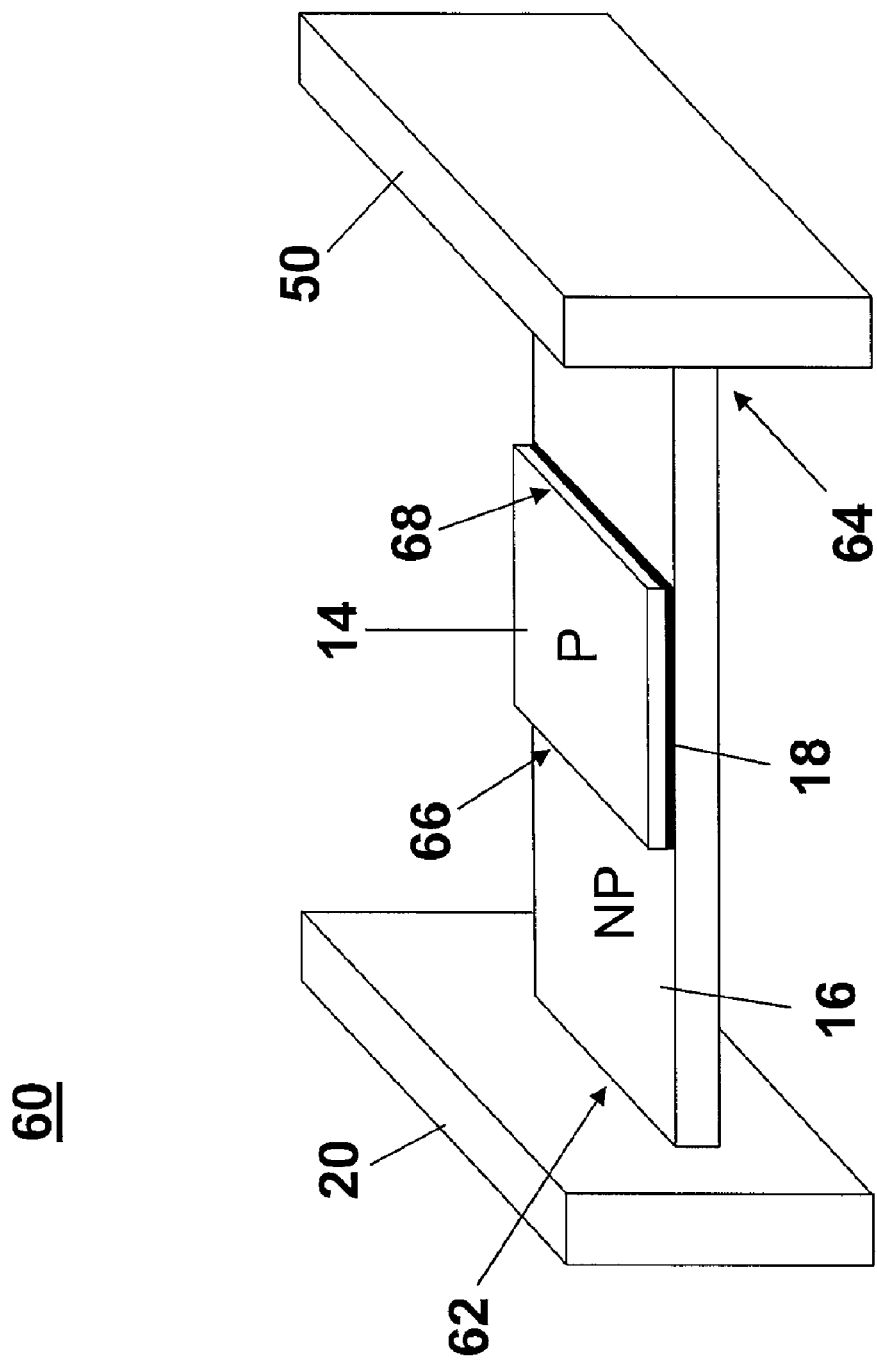
FIG. 8 is an illustration of another example configuration of a self-exciting, self-sensing piezoelectric cantilever sensor, wherein the piezoelectric layer is not attached to either base portion.

FIG. 8 is an illustration of an example configuration 60 of an anchored self-exciting, self-sensing piezoelectric cantilever sensor comprising two base portions 20, 50, wherein the piezoelectric portion 14 is not attached to either base portion 20 or base portion 50. In the configuration depicted in the self-exciting, self-sensing piezoelectric cantilever sensor 60, the proximate end 62 of the non-piezoelectric portion 16 is attached to the base portion 20 and the distal end 64 of the non-piezoelectric portion 16 is attached to the base portion 50. The proximate end 62 of the non-piezoelectric portion 16 extends beyond the proximate end 66 of the piezoelectric portion 14 and the distal end 64 of the non-piezoelectric portion 16 extends beyond the distal end 68 of the piezoelectric portion 14. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 9:
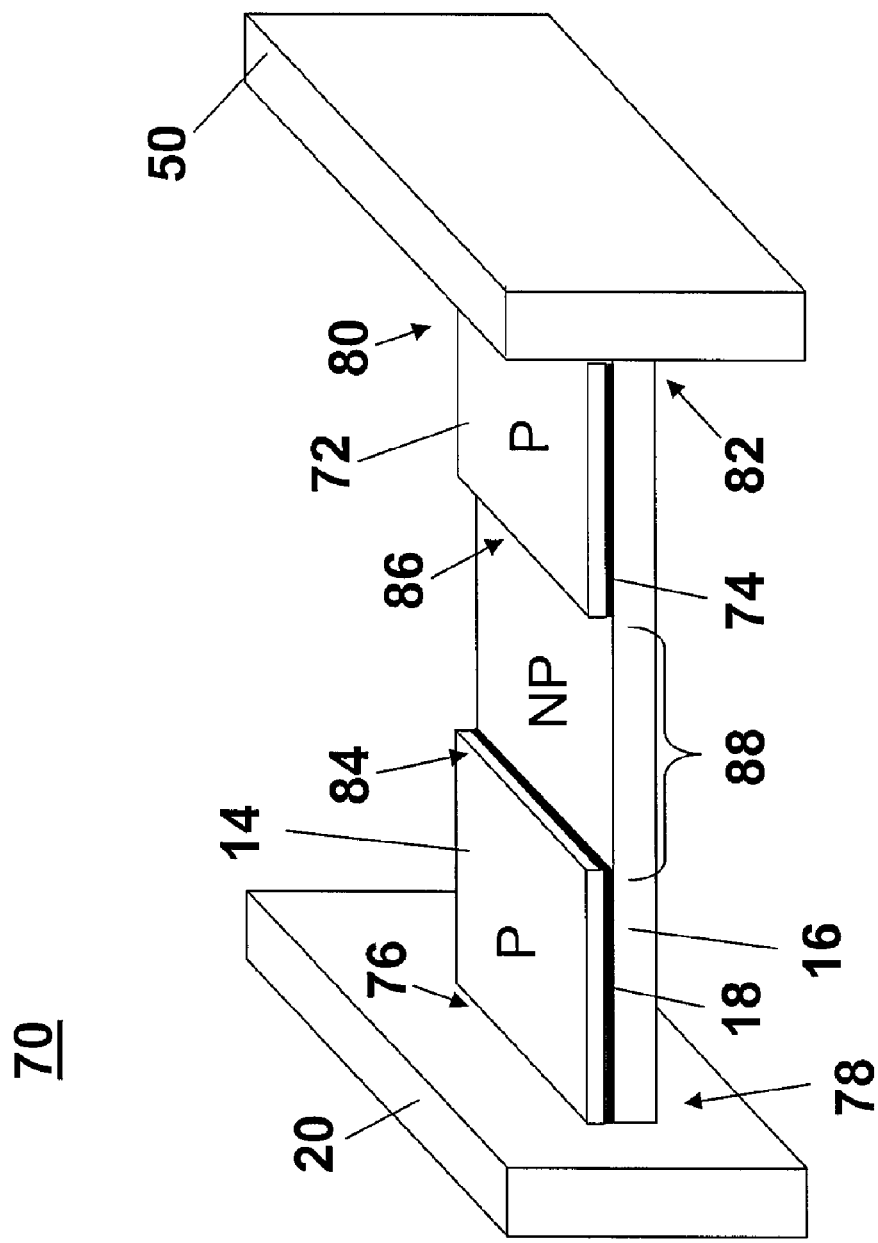
FIG. 9 is an illustration of an example configuration of a self-exciting, self-sensing piezoelectric cantilever sensor having the piezoelectric layer anchored at two ends.

FIG. 9 is an illustration of an example configuration 70 of an anchored self-exciting, self-sensing piezoelectric cantilever sensor comprising two base portions 20, 50, comprising two piezoelectric portions 14, 72, and comprising two adhesive portions 18, 74. In the configuration depicted in the self-exciting, self-sensing piezoelectric cantilever sensor 70, the proximate end 76 of the piezoelectric portion 14 and the proximate end 78 of the non-piezoelectric portion 16 are attached to the base portion 20. The distal end 80 of the piezoelectric portion 72 and the distal end 82 of the non-piezoelectric portion 16 are attached to the base portion 50. The proximate end 78 of the non-piezoelectric portion 16 extends beyond the proximate end 86 of the piezoelectric portion 72. The distal end 82 of the non-piezoelectric portion 16 extends beyond the distal end 84 of the piezoelectric portion 14. The distal end 84 of the piezoelectric portion 14 and the proximate end 86 of the piezoelectric portion 72 form a space 88 therebetween. The piezoelectric portion 14 is coupled to the non-piezoelectric portion 16 via adhesive portion 18. The piezoelectric portion 72 is coupled to the non-piezoelectric portion 16 via adhesive portion 74. The adhesive portions 18 and 74 are positioned, respectively, between the overlapping portions of the piezoelectric portion 14 and the non-piezoelectric portion 16, and the piezoelectric portion 72 and the non-piezoelectric portion 16.

Figure 10:
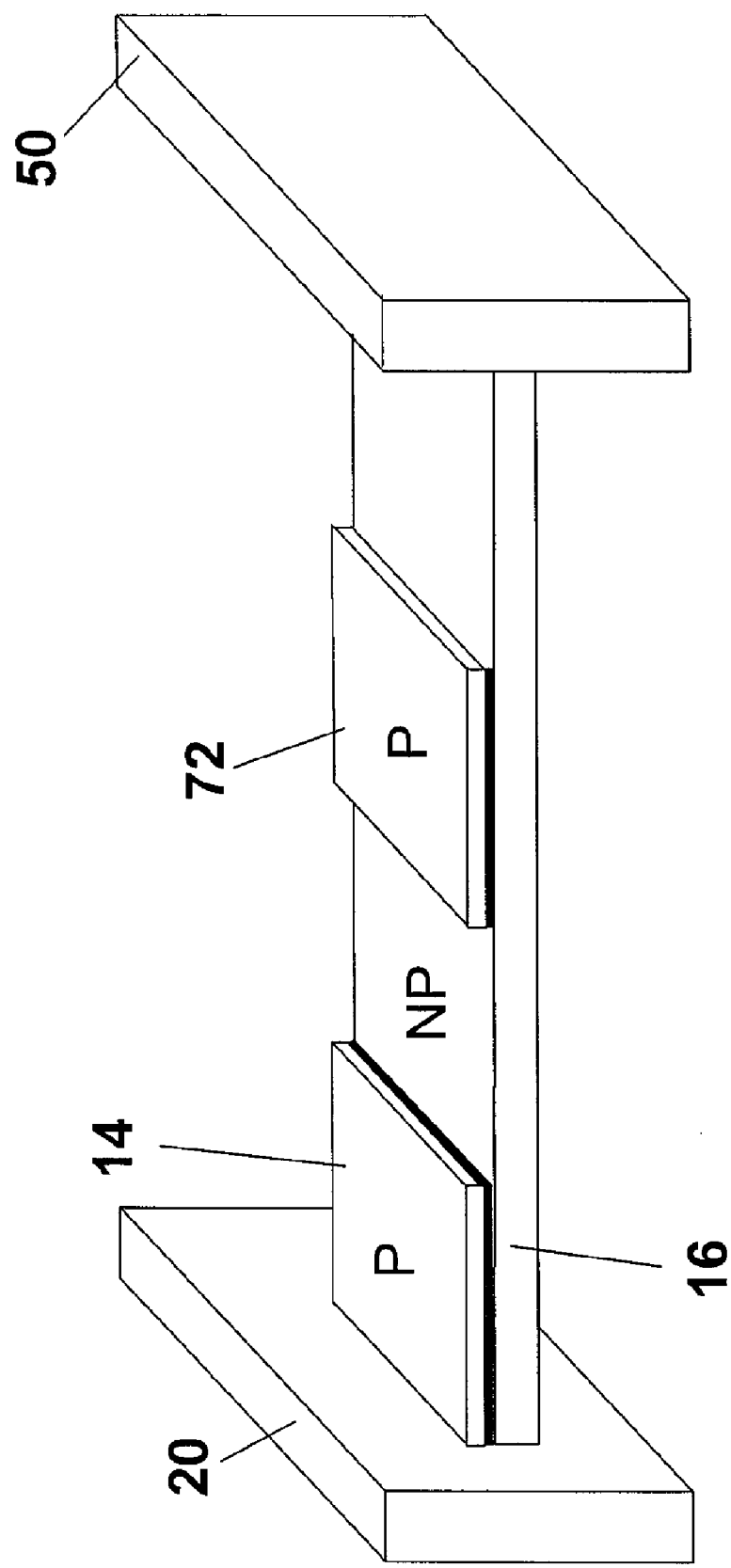
FIG. 10 is an illustration of an example configuration of a self-exciting, self-sensing piezoelectric cantilever sensor wherein the piezoelectric layer comprises two portions, one of which is anchored.
Figure 11:
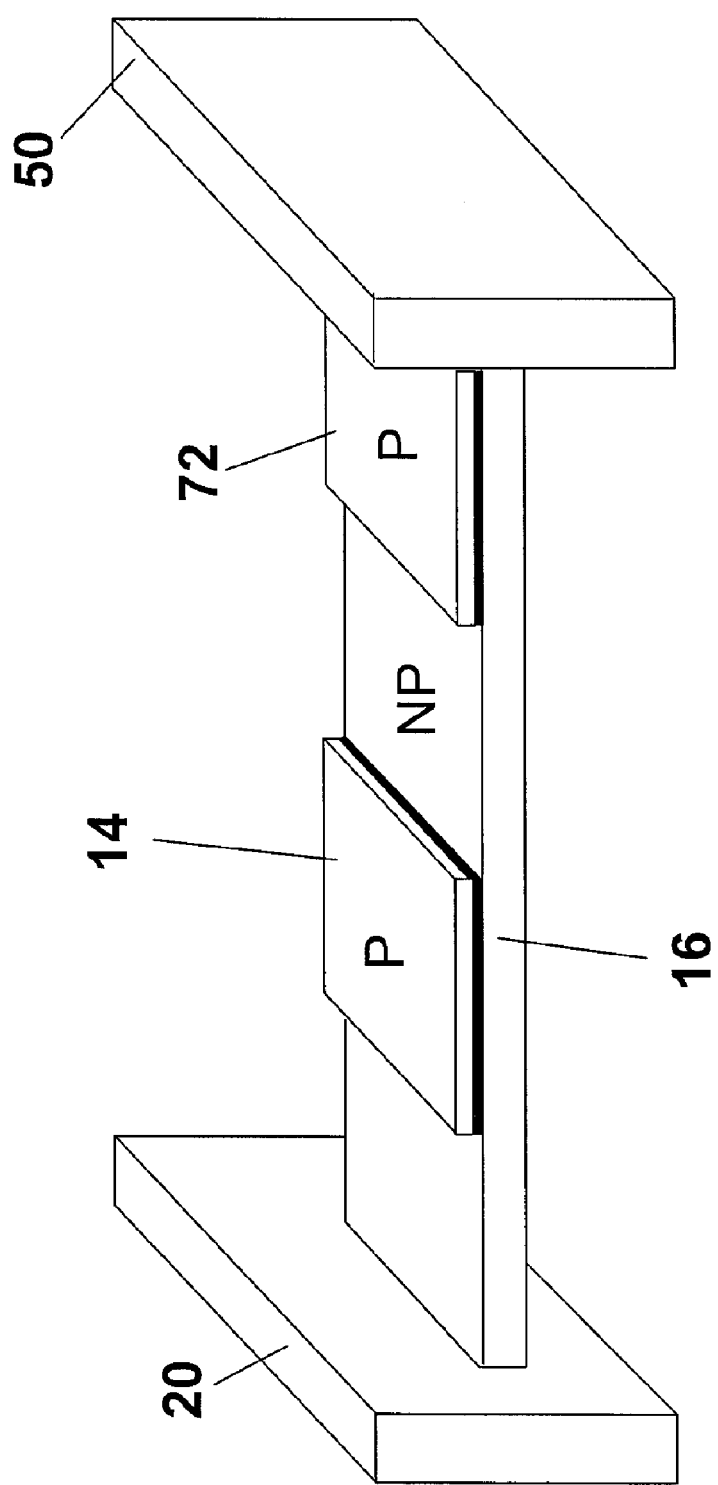
FIG. 11 is another illustration of an example configuration of a self-exciting, self-sensing piezoelectric cantilever sensor wherein the piezoelectric layer comprises two portions, one of which is anchored.
Figure 12:
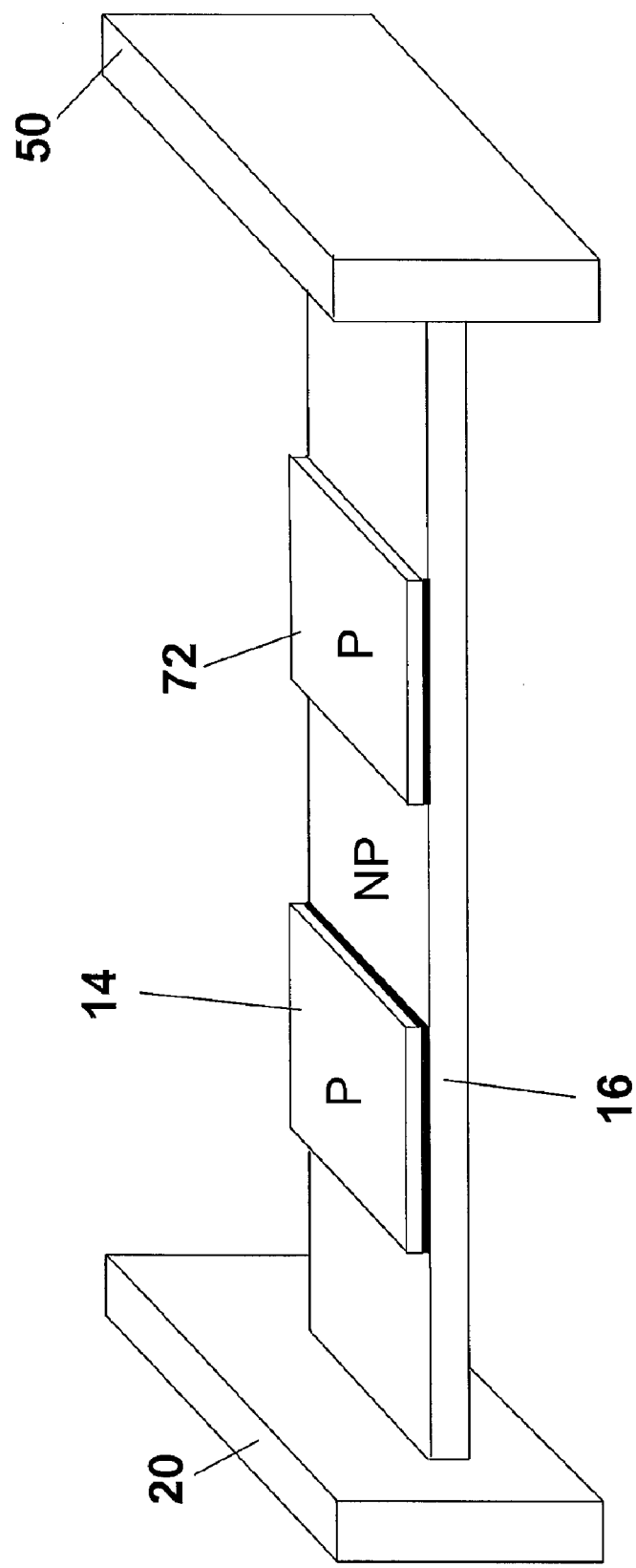
FIG. 12 is an illustration of an example configuration of a self-exciting, self-sensing piezoelectric cantilever sensor wherein the piezoelectric layer comprises two portions, neither which is anchored.

In various alternate example configurations of the configuration 70 depicted in FIG. 9, only one of the piezoelectric portions 14, 72 is attached to a respective base portion 20, 50. For example, in one example configuration as depicted in FIG. 10, the piezoelectric portion 14 is attached to the base portion 20 and the piezoelectric portion 72 is not attached to the base portion 50. In another example configuration, as depicted in FIG. 11, the piezoelectric portion 72 is attached to the base portion 50 and the piezoelectric portion 14 is not attached to the base portion 20. In yet another example configuration, as depicted in FIG. 12, neither the piezoelectric portion 14 nor the piezoelectric portion 72 is attached to a respective base portion 20, 50. In the various example configurations in which a piezoelectric layer comprises multiple portions, electrodes can be attached to any appropriate piezoelectric portion or portions. For example, in the example configuration depicted in FIG. 9, FIG. 10, FIG. 11, and FIG. 12, electrodes can be attached to piezoelectric portion 14, piezoelectric portion 72, or a combination thereof.

Figure 13:
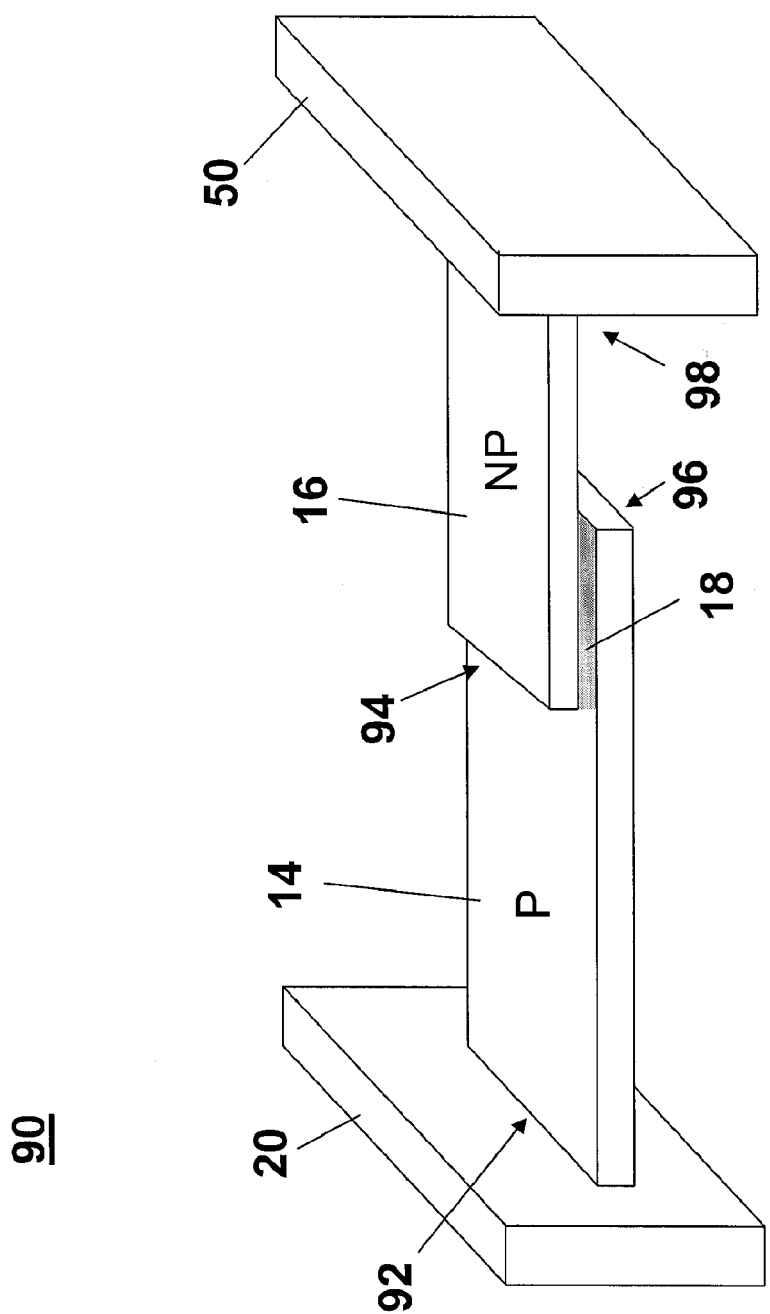
FIG. 13 is an illustration of an example configuration of a self-exciting, self-sensing piezoelectric cantilever sensor having an anchored non-piezoelectric portion and a non-anchored piezoelectric portion.

FIG. 13 is an illustration of an example configuration 90 of an anchored self-exciting, self-sensing piezoelectric cantilever sensor comprising two base portions 20, 50, wherein the piezoelectric portion 14 is attached to the base portion 20 and the non-piezoelectric portion 16 is attached to the base portion 50. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The distal end 98 of the non-piezoelectric portion 16 extends beyond the distal end 96 of the piezoelectric portion 14. The proximate end 92 of the piezoelectric portion 14 extends beyond the proximate end 94 of the non-piezoelectric portion 16.

Figure 14:
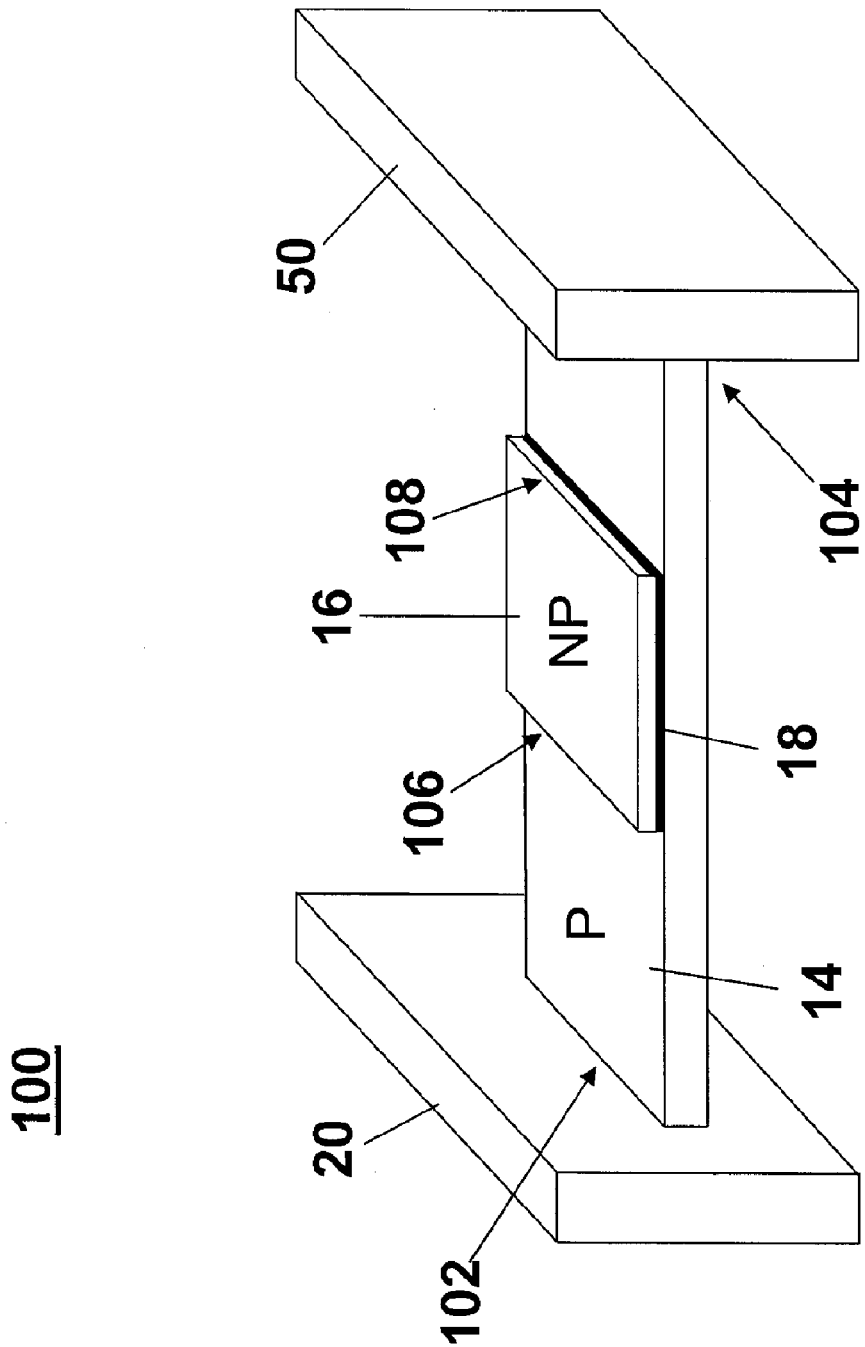
FIG. 14 is an illustration of an example configuration of a self-exciting, self-sensing piezoelectric cantilever sensor, wherein the non-piezoelectric layer is not attached to either base portion.

FIG. 14 is an illustration of an example configuration 100 of an anchored self-exciting, self-sensing piezoelectric cantilever sensor comprising two base portions 20, 50, wherein the non-piezoelectric portion 16 is not attached to either base portion 20 or base portion 50. In the configuration depicted in the self-exciting, self-sensing piezoelectric cantilever sensor 100, the proximate end 102 of the piezoelectric portion 14 is attached to the base portion 20 and the distal end 104 of the piezoelectric portion 14 is attached to the base portion 50. The proximate end 102 of the piezoelectric portion 14 extends beyond the proximate end 106 of the non-piezoelectric portion 16 and the distal end 104 of the piezoelectric portion 14 extends beyond the distal end 108 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 15:
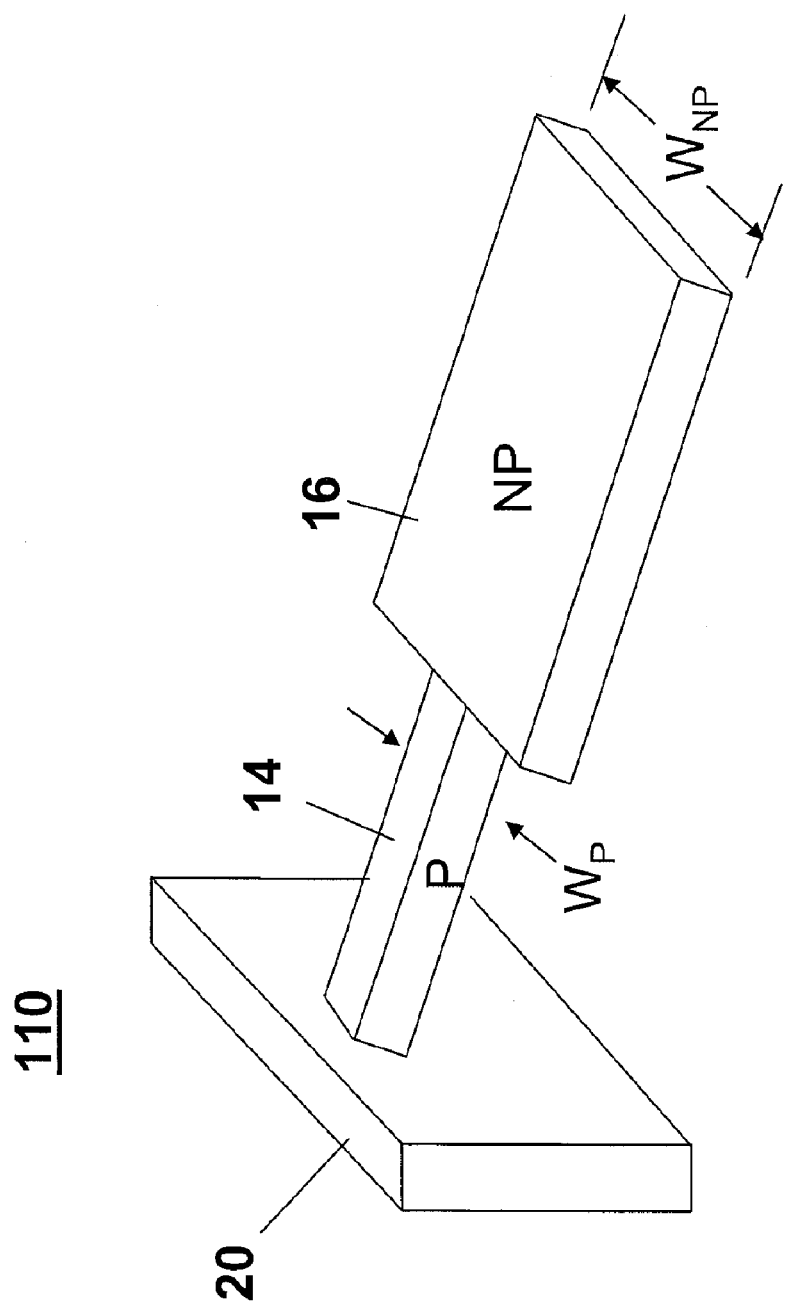
FIG. 15 is illustration of another example configuration of a self-exciting, self-sensing piezoelectric cantilever sensor wherein the piezoelectric portion has a different width than the piezoelectric portion.

FIG. 15 is an illustration of an example configuration 110 of an unanchored self-exciting, self-sensing piezoelectric cantilever sensor comprising a piezoelectric portion 14 and a non-piezoelectric portion 16, wherein the width, $W_P$, of the piezoelectric portion is less than the width, $W_{NP}$, of the non-piezoelectric portion 16. The configuration 110 depicted in FIG. 15 is similar to the configuration 12 depicted in FIG. 1, with the exception that $W_P$ is less than $W_{NP}$. According, the self-exciting, self-sensing piezoelectric cantilever sensor 110 depicts an embodiment of an unanchored, overhang, self-exciting, self-sensing piezoelectric cantilever sensor. The piezoelectric portion 14 is coupled to the non-piezoelectric portion 16 via adhesive portion (adhesive portion not shown in FIG. 15). The adhesive portion is positioned between the overlapping portions of the piezoelectric portion 14 and the non-piezoelectric portion 16. The piezoelectric portion 14 is coupled to a base portion 20.

Figure 16:
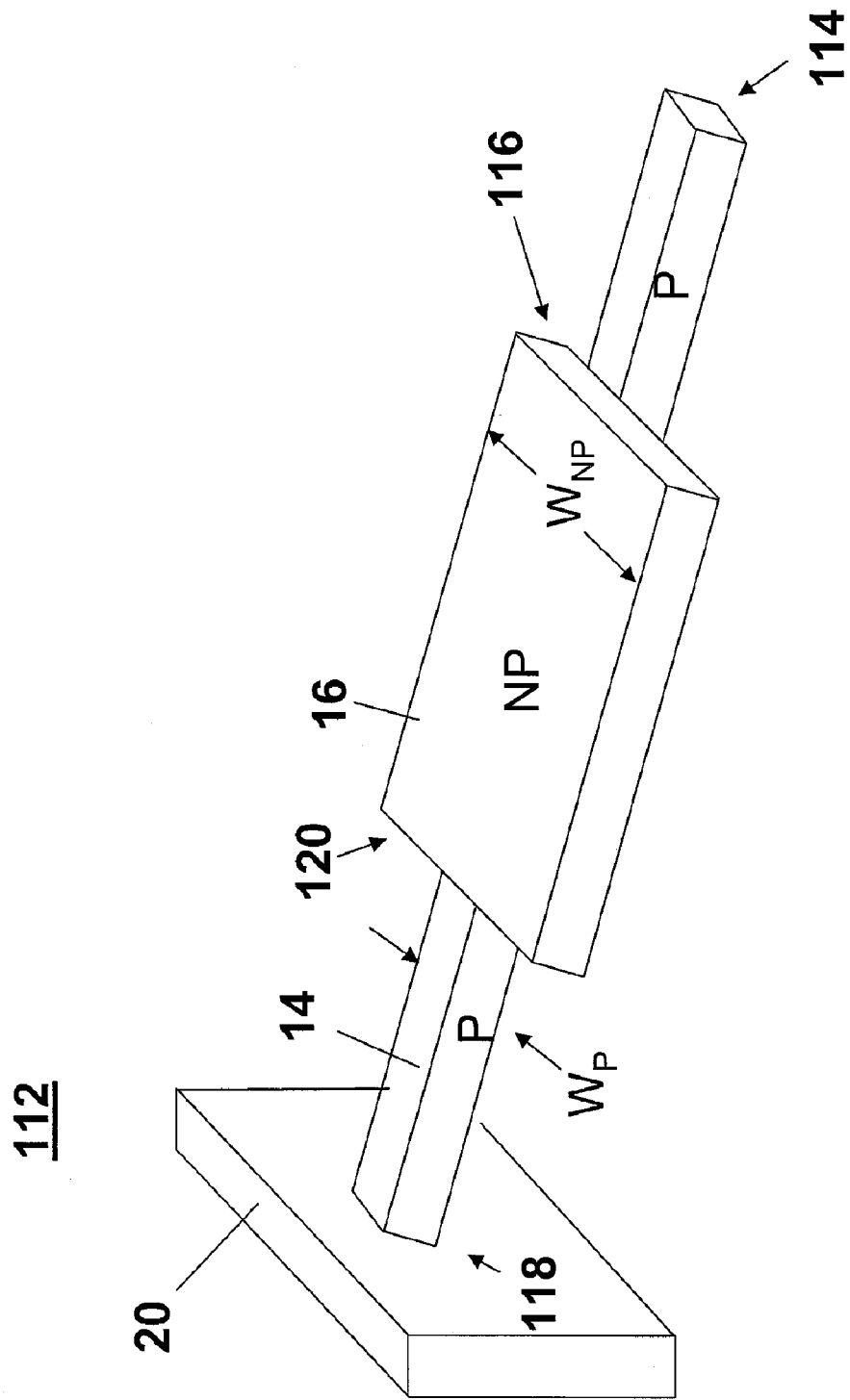
FIG. 16 is an illustration of an example configuration of a self-exciting, self-sensing piezoelectric cantilever sensor comprising a piezoelectric layer and a non-piezoelectric layer, wherein the width, of the piezoelectric layer is less than the width of the non-piezoelectric layer 16, and the distal end of the piezoelectric layer extends beyond the distal end of the non-piezoelectric layer and the proximate end of the piezoelectric layer extends beyond the proximate end of the non-piezoelectric layer.

FIG. 16 is an illustration of an example configuration 112 of an unanchored self-exciting, self-sensing piezoelectric cantilever sensor comprising a piezoelectric portion 14 and a non-piezoelectric portion 16, wherein the width, $W_P$, of the piezoelectric portion is less than the width, $W_{NP}$, of the non-piezoelectric portion 16, and wherein the distal end 114 of the piezoelectric portion 14 extends beyond the distal end 116 of the non-piezoelectric portion 16 and the proximate end 118 of the piezoelectric portion 14 extends beyond the proximate end 120 of the non-piezoelectric portion 16. The configuration 112 depicted in FIG. 16 is similar to the configuration 42 depicted in FIG. 6, with the exception that $W_P$ is less than $W_{NP}$. The piezoelectric portion 14 is coupled to the non-piezoelectric portion 16 via adhesive portion (adhesive portion not shown in FIG. 16). The adhesive portion is positioned between the overlapping portions of the piezoelectric portion 14 and the non-piezoelectric portion 16. The piezoelectric portion 14 is coupled to the base portion 20.

Figure 17:
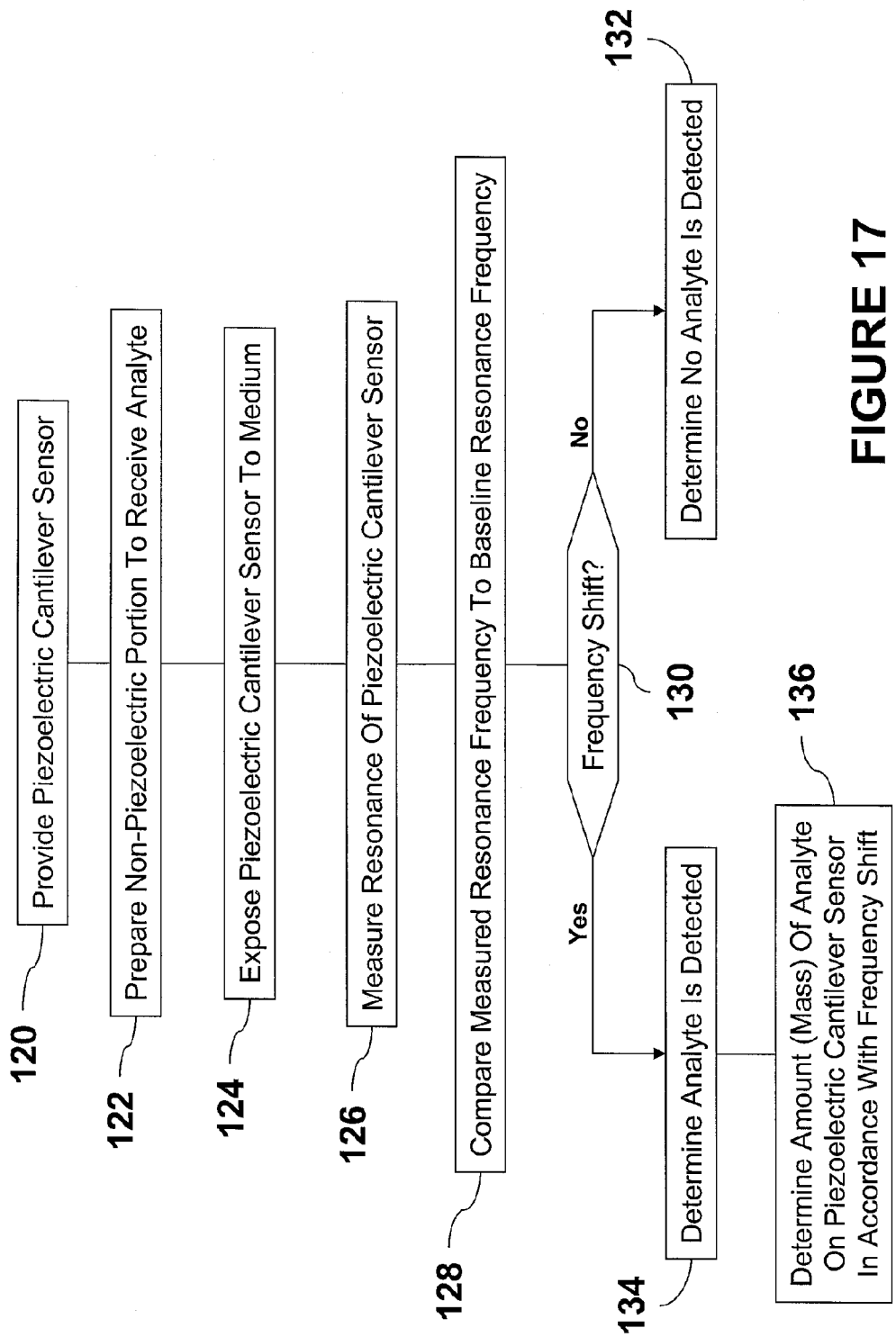
FIG. 17 is a flow diagram of an example process for detecting an analyte utilizing the self-exciting, self-sensing piezoelectric cantilever sensor.

FIG. 17 is a flow diagram of an example process for detecting an analyte utilizing the self-exciting, self-sensing piezoelectric cantilever sensor. The self-exciting, self-sensing piezoelectric cantilever sensor is provided at step 120. The self-exciting, self-sensing piezoelectric cantilever sensor can be configured in accordance with the descriptions provided above, or configured in accordance with any appropriate variant is thereof. The self-exciting, self-sensing piezoelectric cantilever sensor is prepared to receive an analyte at step 122. In an example embodiment, an analyte attractor is applied to the non-piezoelectric portion of the self-exciting, self-sensing piezoelectric cantilever sensor. The attractor is specific to an analyte. Thus the attractor will attract a target analyte and not attract other substances. For example, the non-piezoelectric portion of the self-exciting, self-sensing piezoelectric cantilever sensor can comprise an attractor for attracting bio-terrorism agents, such as *Bacillus anthracis*, food-borne pathogens, such as *E. coli*, pathogens in food and water, cell types in body fluids (e.g., circulating tumor cells), biomarkers in body fluids (e.g., proteins that mark specific pathophysiology-alpha-fetoprotein, beta-2-microglobulin, bladder tumor antigen, breast cancer marker CA-15-3, and other CAs (cancer antigens), calcitonin, carcinoembryonic antigen, and others), markers of explosives such as trinitrotoluene, dinitrotoluene, airborne and waterborne toxins, biological entities, such as a protein, or a combination thereof, for example.

The self-exciting, self-sensing piezoelectric cantilever sensor is exposed to a medium at step 124. The medium can comprise any appropriate medium, such as a liquid, a gas, a combination of a liquid and a gas, or a vacuum, for example. The medium can exhibit a wide variety of flow conditions. If a target analyte is present in the medium, the target analyte will accumulate on the non-piezoelectric portion of the self-exciting, self-sensing piezoelectric cantilever sensor that has been treated with the attractor. As described above, accumulation (e.g., binding) of the target analyte on the non-piezoelectric portion of the self-exciting, self-sensing piezoelectric cantilever sensor will result in a change in stiffness of the self-exciting, self-sensing piezoelectric cantilever sensor and/or an increase the mass of the self-exciting, self-sensing piezoelectric cantilever sensor, which will decrease the resonance frequency of the self-exciting, self-sensing piezoelectric cantilever sensor.

The resonance frequency of the self-exciting, self-sensing piezoelectric cantilever sensor is measure at step 126. The resonance frequency can be measured by any appropriate means, such as an operational amplifier, an impedance analyzer, a network analyzer, an oscillator circuit, or the like, for example. When the piezoelectric material of the piezoelectric portion of the self-exciting, self-sensing piezoelectric cantilever sensor is excited, the non-piezoelectric portion of the self-exciting, self-sensing piezoelectric cantilever sensor flexes to accommodate the strain caused in the piezoelectric material. When the frequency of excitation is the same as the natural frequency of the underlying mechanical structure, resonance occurs.

The measured resonance frequency is compared to a baseline resonance frequency at step 128. The baseline resonance frequency is the resonance frequency of the self-exciting, self-sensing piezoelectric cantilever sensor having no analyte accumulated thereon. If a difference in frequency (frequency shift) between the measured resonance frequency and the baseline resonance frequency is not measured (at step 130), it is determined, at step 132, that no analyte is detected. If a difference in frequency between the measured resonance frequency and the baseline resonance frequency is measured (at step 130), it is determined, at step 134, that an analyte is detected, i.e., an analyte is present in the medium. At step 136, the amount of mass of the analyte that has accumulated on the non-piezoelectric portion of the self-exciting, self-sensing piezoelectric cantilever sensor is determined in accordance with the frequency shift measured at step 130.

Figure 18:
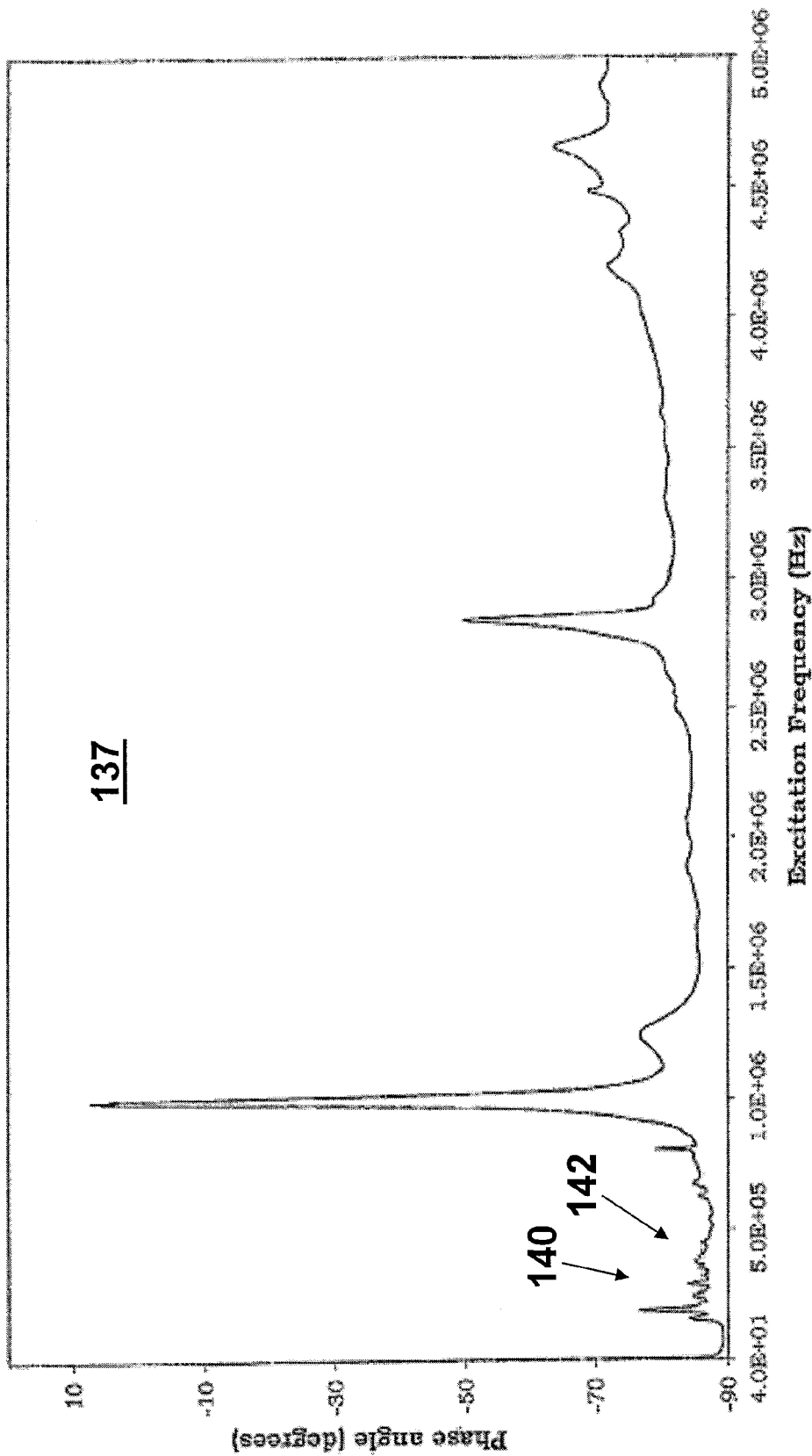
FIG. 18 is a plot of an example resonance spectrum of the configuration of the self-exciting, self-sensing piezoelectric cantilever sensor depicted in FIG. 1, operated in air.

Various experiments have been conducted utilizing various configurations of the self-exciting, self-sensing piezoelectric cantilever sensor. FIG. 18 is a plot 137 of an example resonance spectrum of the configuration 12 of the self-exciting, self-sensing piezoelectric cantilever sensor, depicted in FIG. 1, operated in air. The width, $W_P$, and the width, $W_{NP}$, were each approximately 2 mm. The plot 137 shows the phase angle (between the excitation voltage and the excitation current) versus excitation frequency, at an excitation voltage of 100 mV. The first resonance frequency mode 140 occurred approximately between 150 and 200 kHz and the second resonance frequency mode 142 occurred between 250 and 300 kHz. The resonance spectrum shows higher order characteristic peaks at approximately 980 kHz, 2.90 MHz and 4.60 MHz.

Quality factors were determined as a ratio of the resonant frequency to the peak width at half the peak height. As a result, the quality factor is a measure of the sharpness of the resonant peaks. Experimentation has shown that the quality factor of the self-exciting, self-sensing piezoelectric cantilever sensor does not decrease significantly when the sensor is placed in different environments ranging from vacuum to liquid flow environments. Also, experimentation has shown that the Q values for the various configurations of the self-exciting, self-sensing piezoelectric cantilever sensor typically range between 10 and 70, depending upon the respective frequency mode where the peak is detected. The various configurations of the self-exciting, self-sensing piezoelectric cantilever sensor, when used in vacuum, air, and viscous environments, including flows, typically did not have more than a 20%-35% decrease in Q value. This relatively small loss in the overall value of the quality factor reflects the ability of the self-exciting, self-sensing piezoelectric cantilever sensor to accurately detect chemicals and various biological items in viscous environments, including water and bloodstreams.

Experimentation has shown that the sensitivity of the self-exciting, self-sensing piezoelectric cantilever sensor is a function of the dimensions thereof. Specific changes in the geometry of the self-exciting, self-sensing piezoelectric cantilever sensor enhanced the sensor's mass change sensitivity, and thus, the sensor's response to the detection of low concentration of analyte. The resonance spectrum, a plot of phase angle versus excitation frequency, in air, showed dominant bending mode resonant peaks at 102±0.05, 970±0.05, and 1810±0.05 kHz, respectively. By changing the geometry of the of the self-exciting, self-sensing piezoelectric cantilever sensor, the sensor's resonance characteristics were enhanced. The corresponding bending resonant modes occurred at higher frequencies and had larger phase angles, suggesting that resonant peaks of the self-exciting, self-sensing piezoelectric cantilever sensor are more sensitive and are less dampened.

In an example experiment, the mass change sensitivity of the self-exciting, self-sensing piezoelectric cantilever sensor was measured. A known mass of paraffin wax was added to a glass surface of the self-exciting, self-sensing piezoelectric cantilever sensor and the change in resonant frequency was used to compute the mass sensitivity, expressed in g/Hz. Direct measurement was made of the mass change sensitivity in liquid; as well as the ratio of known mass to the change in resonant frequency in liquid before and after mass was added. The mass sensitivity of the resonant mode investigated under liquid was determined to be $1.5 \times 10^{-15}$ g/Hz.

What is claimed:

1. A cantilever sensor comprising:
   a piezoelectric layer comprising a proximate end and a distal end;
   a base portion coupled to the proximate end of the piezoelectric layer;
   a non-piezoelectric layer comprising a proximate end and a distal end, wherein:
      at least a portion of the piezoelectric layer is coupled to at least a portion of the non-piezoelectric layer such that the piezoelectric layer and the non-piezoelectric layer are not coextensive; and
      the base portion is not attached to the non-piezoelectric layer; and
   electrodes operatively associated with the piezoelectric layer.

2. A sensor in accordance with claim 1, wherein:
   the distal end of the non-piezoelectric layer extends beyond the distal end of the piezoelectric layer; and
   the proximate end of the piezoelectric layer extends beyond the proximate end of the non-piezoelectric layer.

3. A sensor in accordance with claim 1, wherein:
   the distal end of the non-piezoelectric layer is flush with the distal end of the piezoelectric layer; and
   the proximate end of the piezoelectric layer extends beyond the proximate end of the non-piezoelectric layer.

4. A sensor in accordance with claim 1, wherein the non-piezoelectric layer comprises at least one of glass, a ceramic, a metal, a polymer, and a polymer and a ceramic composite.

5. A sensor in accordance with claim 1, wherein the non-piezoelectric layer comprises at least one of silicon dioxide, copper, stainless steel, and titanium.

6. A sensor in accordance with claim 1, wherein the piezoelectric layer comprises at least one of lead zirconate titanate, lead magnesium niobate-lead titanate solid solutions, strontium lead titanate, quartz silica, piezoelectric ceramic lead zirconate and titanate (PZT), and a piezoceramic-polymer fiber composite.

7. A sensor in accordance with claim 1, wherein a length of the non-piezoelectric layer is in a range of about 0.1 mm to about 10.0 mm.

8. A sensor in accordance with claim 1, wherein a length of the piezoelectric layer is in a range of about 0.1 mm to about 10.0 mm.

9. A sensor in accordance with claim 1, wherein a width of the non-piezoelectric layer is in a range of about 0.1 mm to about 4.0 mm.

10. A sensor in accordance with claim 1, wherein a width of the piezoelectric layer is in a range of about 0.1 mm to about 4.0 mm.

11. A sensor in accordance with claim 1, wherein at least one physical dimension of at least one of the piezoelectric layer and the non-piezoelectric layer is non-uniform.

12. A sensor in accordance with claim 1, wherein the electrodes are utilized to measure a resonance frequency of the sensor.

13. A sensor in accordance with claim 12, wherein the measured resonance frequency is indicative of an amount of analyte accumulated on the sensor.

14. A sensor in accordance with claim 1, wherein:
   oscillation associated stress is concentrated in the piezoelectric layer near the base portion; and
   the electrodes are positioned proximate to a location of the concentrated stress.

15. A sensor in accordance with claim 1, wherein:
   the distal end of the piezoelectric layer extends beyond the distal end of the non-piezoelectric layer; and
   the proximate end of the piezoelectric layer extends beyond the proximate end of the non-piezoelectric layer.

* * * * *